(12) United States Patent
Gera et al.

(10) Patent No.: US 12,150,821 B2
(45) Date of Patent: Nov. 26, 2024

(54) ROTATING MARKER AND ADAPTER FOR IMAGE-GUIDED SURGERY

(71) Applicant: AUGMEDICS LTD., Yokneam Illit (IL)

(72) Inventors: Tomer Gera, Kfar Tavor (IL); Nissan Elimelech, Beerotaim (IL)

(73) Assignee: AUGMEDICS LTD., Yokneam Illit (IL)

( * ) Notice: Subject to any disclaimer, the term of this patent is extended or adjusted under 35 U.S.C. 154(b) by 645 days.

(21) Appl. No.: 17/388,064

(22) Filed: Jul. 29, 2021

(65) Prior Publication Data

US 2023/0034189 A1    Feb. 2, 2023

(51) Int. Cl.
*A61B 90/00*    (2016.01)

(52) U.S. Cl.
CPC ...... *A61B 90/39* (2016.02); *A61B 2090/3916* (2016.02); *A61B 2090/3966* (2016.02); *A61B 2090/3983* (2016.02); *A61B 2090/3991* (2016.02)

(58) Field of Classification Search
CPC ............ A61B 90/39; A61B 2090/3983; A61B 2090/3991
See application file for complete search history.

(56) References Cited

U.S. PATENT DOCUMENTS

| | | |
|---|---|---|
| 3,690,776 A | 9/1972 | Zaporoshan |
| 4,459,358 A | 7/1984 | Berke |
| 4,711,512 A | 12/1987 | Upatnieks |
| 4,863,238 A | 9/1989 | Brewster |
| 4,944,739 A | 7/1990 | Torre |
| 5,357,292 A | 10/1994 | Wiedner |

(Continued)

FOREIGN PATENT DOCUMENTS

| | | |
|---|---|---|
| CA | 3022448 A1 | 2/2018 |
| CA | 3034314 A1 | 2/2018 |

(Continued)

OTHER PUBLICATIONS

US 11,395,705 B2, 09/2022, Lang (withdrawn)

(Continued)

*Primary Examiner* — Keith M Raymond
*Assistant Examiner* — Johnathan Maynard
(74) *Attorney, Agent, or Firm* — KNOBBE, MARTENS, OLSON & BEAR, LLP

(57) ABSTRACT

A patient marker couples to an anchoring device via a base having a base axis, base connections and a first indicator. The marker includes: an adapter having a first surface with connections configured to mate with the base connections, and a second surface with connections congruent with the base connections, and at least one second indicator. The marker includes an alignment target, having a target region with an alignment pattern, and a socket connected to the target region with socket connections congruent with the first surface connections. In a first configuration the socket couples to the base by mating the first surface connections with the base connections and mating the socket connections with the second surface connections. In a second configuration, the socket fits onto the base by mating the socket connections with the base connections. One of the indicators indicates a target orientation angle about the base axis.

18 Claims, 9 Drawing Sheets

(56) References Cited

U.S. PATENT DOCUMENTS

| | | |
|---|---|---|
| 5,441,042 A | 8/1995 | Putman |
| 5,442,146 A | 8/1995 | Bell |
| 5,510,832 A | 4/1996 | Garcia |
| D370,309 S | 5/1996 | Stucky |
| 5,636,255 A | 6/1997 | Ellis |
| 5,665,092 A | 9/1997 | Mangiardi et al. |
| 5,771,121 A | 6/1998 | Hentschke |
| 5,792,046 A | 8/1998 | Dobrovolny |
| 5,841,507 A | 11/1998 | Barnes et al. |
| 6,006,126 A | 12/1999 | Cosman |
| 6,038,467 A | 3/2000 | De Bliek et al. |
| 6,125,164 A | 9/2000 | Murphy |
| 6,147,805 A | 11/2000 | Fergason |
| 6,227,667 B1 | 5/2001 | Halldorsson |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,449,090 B1 | 9/2002 | Omar |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa |
| 6,578,962 B1 | 6/2003 | Amir et al. |
| 6,609,022 B2 | 8/2003 | Vilsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto |
| 6,740,882 B2 | 5/2004 | Weinberg |
| 6,757,068 B2 | 6/2004 | Foxlin |
| 6,759,200 B1 | 7/2004 | Stanton |
| 6,847,336 B1 | 1/2005 | Lemelson et al. |
| 6,856,324 B2 | 2/2005 | Sauer |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,000,262 B2 | 2/2006 | Bielefeld |
| 7,035,371 B2 | 4/2006 | Boese et al. |
| 7,043,961 B2 | 5/2006 | Pandey et al. |
| 7,072,435 B2 | 7/2006 | Metz et al. |
| 7,103,233 B2 | 9/2006 | Stearns |
| 7,107,091 B2 | 9/2006 | Jutras et al. |
| 7,112,656 B2 | 9/2006 | Desnoyers |
| 7,141,812 B2 | 11/2006 | Appleby |
| 7,157,459 B2 | 1/2007 | Ohta |
| 7,169,785 B2 | 1/2007 | Timmer |
| 7,171,255 B2 | 1/2007 | Holupka et al. |
| 7,176,936 B2 | 2/2007 | Sauer et al. |
| 7,187,792 B2 | 3/2007 | Fu |
| 7,190,331 B2 | 3/2007 | Genc et al. |
| 7,194,295 B2 | 3/2007 | Vilsmeier |
| 7,215,322 B2 | 5/2007 | Genc et al. |
| 7,229,078 B2 | 6/2007 | Lechot |
| 7,231,076 B2 | 6/2007 | Fu |
| 7,235,076 B2 | 6/2007 | Pacheco |
| 7,239,330 B2 | 7/2007 | Sauer et al. |
| 7,259,266 B2 | 8/2007 | Carter |
| 7,260,426 B2 | 8/2007 | Schweikard |
| 7,269,192 B2 | 9/2007 | Hayashi |
| 7,281,826 B2 | 10/2007 | Huang |
| 7,315,636 B2 | 1/2008 | Kuduvalli |
| 7,320,556 B2 | 1/2008 | Vagn-Erik |
| 7,330,578 B2 | 2/2008 | Wang |
| 7,359,535 B2 | 4/2008 | Salla |
| 7,364,314 B2 | 4/2008 | Nilsen et al. |
| 7,366,934 B1 | 4/2008 | Narayan et al. |
| 7,379,077 B2 | 5/2008 | Bani-Hashemi |
| 7,431,453 B2 | 10/2008 | Hogan |
| 7,435,219 B2 | 10/2008 | Kim |
| 7,450,743 B2 | 11/2008 | Sundar et al. |
| 7,458,977 B2 | 12/2008 | McGinley |
| 7,462,852 B2 | 12/2008 | Appleby |
| 7,493,153 B2 | 2/2009 | Ahmed et al. |
| 7,505,617 B2 | 3/2009 | Fu |
| 7,507,968 B2 | 3/2009 | Wollenweber |
| 7,518,136 B2 | 4/2009 | Appleby |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire et al. |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton |
| 7,570,791 B2 | 8/2009 | Frank et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson |
| 7,620,223 B2 | 11/2009 | Xu |
| 7,623,902 B2 | 11/2009 | Pacheco |
| 7,627,085 B2 | 12/2009 | Boyden et al. |
| 7,630,753 B2 | 12/2009 | Simon et al. |
| 7,633,501 B2 | 12/2009 | Wood |
| 7,645,050 B2 | 1/2010 | Wilt |
| 7,653,226 B2 | 1/2010 | Guhring et al. |
| 7,657,075 B2 | 2/2010 | Viswanathan |
| 7,689,019 B2 | 3/2010 | Boese |
| 7,689,042 B2 | 3/2010 | Brunner |
| 7,689,320 B2 | 3/2010 | Prisco |
| 7,699,486 B1 | 4/2010 | Beiner |
| 7,699,793 B2 | 4/2010 | Gotte |
| 7,719,769 B2 | 5/2010 | Sugihara et al. |
| D617,825 S | 6/2010 | Chang |
| 7,734,327 B2 | 6/2010 | Colquhoun |
| D619,285 S | 7/2010 | Cristoforo |
| 7,751,865 B2 | 7/2010 | Jascob et al. |
| 7,758,204 B2 | 7/2010 | Klipstein |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,073 B2 | 11/2010 | Fu et al. |
| 7,831,096 B2 | 11/2010 | Williamson |
| 7,835,778 B2 | 11/2010 | Foley |
| 7,835,784 B2 | 11/2010 | Mire et al. |
| 7,837,987 B2 | 11/2010 | Shi |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon |
| 7,854,705 B2 | 12/2010 | Pawluczyk |
| 7,857,271 B2 | 12/2010 | Lees |
| 7,860,282 B2 | 12/2010 | Boese |
| D630,766 S | 1/2011 | Harbin |
| 7,865,269 B2 | 1/2011 | Prisco |
| 7,874,686 B2 | 1/2011 | Rossner et al. |
| 7,881,770 B2 | 2/2011 | Melkent et al. |
| 7,893,413 B1 | 2/2011 | Appleby |
| 7,894,649 B2 | 2/2011 | Fu |
| 7,920,162 B2 | 4/2011 | Masini et al. |
| 7,922,391 B2 | 4/2011 | Essenreiter et al. |

(56) References Cited

U.S. PATENT DOCUMENTS

| | | |
|---|---|---|
| 7,938,553 B1 | 5/2011 | Beiner |
| 7,945,310 B2 | 5/2011 | Gattani |
| 7,953,471 B2 | 5/2011 | Clayton |
| 7,969,383 B2 | 6/2011 | Eberl et al. |
| 7,974,677 B2 | 7/2011 | Mire et al. |
| 7,985,756 B2 | 7/2011 | Barlow |
| 7,991,557 B2 | 8/2011 | Liew |
| 7,993,353 B2 | 8/2011 | Robner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong |
| 8,045,266 B2 | 10/2011 | Nakamura |
| 8,060,181 B2 | 11/2011 | Ponce |
| 8,068,581 B2 | 11/2011 | Boese et al. |
| 8,068,896 B2 | 11/2011 | Daghighian |
| 8,077,943 B2 | 12/2011 | Wiliams |
| 8,079,957 B2 | 12/2011 | Ma et al. |
| 8,081,812 B2 | 12/2011 | Kreiser |
| 8,085,075 B2 | 12/2011 | Huffman |
| 8,085,897 B2 | 12/2011 | Morton |
| 8,090,175 B2 | 1/2012 | Fu |
| 8,092,400 B2 | 1/2012 | Warkentine |
| 8,108,072 B2 | 1/2012 | Zhao |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman |
| 8,180,132 B2 | 5/2012 | Gorges et al. |
| 8,180,429 B2 | 5/2012 | Sasso |
| 8,208,599 B2 | 6/2012 | Ye |
| 8,216,211 B2 | 7/2012 | Mathis et al. |
| 8,221,402 B2 | 7/2012 | Francischelli |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese |
| 8,300,315 B2 | 10/2012 | Kobayashi |
| 8,305,685 B2 | 11/2012 | Heine |
| 8,306,305 B2 | 11/2012 | Porat et al. |
| 8,309,932 B2 | 11/2012 | Haselman |
| 8,317,320 B2 | 11/2012 | Huang |
| 8,328,815 B2 | 12/2012 | Farr et al. |
| 8,335,553 B2 | 12/2012 | Rubner |
| 8,335,557 B2 | 12/2012 | Maschke |
| 8,340,379 B2 | 12/2012 | Razzaque et al. |
| 8,369,925 B2 | 2/2013 | Giesel |
| 8,386,022 B2 | 2/2013 | Jutras et al. |
| 8,394,144 B2 | 3/2013 | Zehavi |
| 8,398,541 B2 | 3/2013 | Dimaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann |
| 8,699,765 B2 | 4/2014 | Hao |
| 8,705,829 B2 | 4/2014 | Frank |
| 8,737,708 B2 | 5/2014 | Hartmann et al. |
| 8,746,887 B2 | 6/2014 | Shestak |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo |
| 8,890,773 B1 | 11/2014 | Pederson |
| 8,890,943 B2 | 11/2014 | Lee |
| 8,897,514 B2 | 11/2014 | Feikas |
| 8,900,131 B2 | 12/2014 | Chopra et al. |
| 8,903,150 B2 | 12/2014 | Star-Lack |
| 8,908,952 B2 | 12/2014 | Isaacs et al. |
| 8,911,358 B2 | 12/2014 | Koninckx et al. |
| 8,917,268 B2 | 12/2014 | Johnsen |
| 8,920,776 B2 | 12/2014 | Gaiger |
| 8,922,589 B2 | 12/2014 | Laor |
| 8,941,559 B2 | 1/2015 | Bar-Zeev et al. |
| 8,942,455 B2 | 1/2015 | Chou |
| 8,950,877 B2 | 2/2015 | Northey et al. |
| 8,953,246 B2 | 2/2015 | Koenig |
| 8,965,583 B2 | 2/2015 | Ortmaier et al. |
| 8,969,829 B2 | 3/2015 | Wollenweber |
| 8,989,349 B2 | 3/2015 | Thomson |
| 8,992,580 B2 | 3/2015 | Bar |
| 8,994,729 B2 | 3/2015 | Nakamura |
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck |
| 9,060,757 B2 | 6/2015 | Lawson et al. |
| 9,066,751 B2 | 6/2015 | Sasso |
| 9,081,436 B1 | 7/2015 | Berme |
| 9,084,635 B2 | 7/2015 | Nuckley et al. |
| 9,085,643 B2 | 7/2015 | Svanborg |
| 9,087,471 B2 | 7/2015 | Miao |
| 9,100,643 B2 | 8/2015 | McDowall |
| 9,101,394 B2 | 8/2015 | Arata et al. |
| 9,104,902 B2 | 8/2015 | Xu et al. |
| 9,111,175 B2 | 8/2015 | Strommer |
| 9,123,155 B2 | 9/2015 | Cunningham et al. |
| 9,125,556 B2 | 9/2015 | Zehavi |
| 9,129,054 B2 | 9/2015 | Nawana et al. |
| 9,129,372 B2 | 9/2015 | Kriston |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 | 10/2015 | Arthur et al. |
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby |
| 9,220,573 B2 | 12/2015 | Kendrick et al. |
| 9,225,895 B2 | 12/2015 | Kozinski |

(56) References Cited

U.S. PATENT DOCUMENTS

| | | |
|---|---|---|
| 9,232,982 B2 | 1/2016 | Soler et al. |
| 9,235,934 B2 | 1/2016 | Mandella |
| 9,240,046 B2 | 1/2016 | Carrell et al. |
| 9,244,278 B2 | 1/2016 | Sugiyama et al. |
| 9,247,240 B2 | 1/2016 | Park |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Ponce |
| 9,286,730 B2 | 3/2016 | Bar-Zeev et al. |
| 9,289,267 B2 | 3/2016 | Sauer et al. |
| 9,300,949 B2 | 3/2016 | Ahearn |
| 9,310,591 B2 | 4/2016 | Hua et al. |
| 9,320,474 B2 | 4/2016 | Demri |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard |
| 9,344,686 B2 | 5/2016 | Moharir |
| 9,349,066 B2 | 5/2016 | Koo |
| 9,349,520 B2 | 5/2016 | Demetriou |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico |
| 9,387,008 B2 | 7/2016 | Sarvestani |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko |
| 9,424,611 B2 | 8/2016 | Kanjirathinkal et al. |
| 9,424,641 B2 | 8/2016 | Wiemker et al. |
| 9,427,286 B2 | 8/2016 | Siewerdsen et al. |
| 9,438,894 B2 | 9/2016 | Park |
| 9,443,488 B2 | 9/2016 | Borenstein |
| 9,453,804 B2 | 9/2016 | Tahtali |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel |
| 9,473,766 B2 | 10/2016 | Douglas |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,499,999 B2 | 11/2016 | Zhou |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme |
| 9,530,382 B2 | 12/2016 | Simmons |
| 9,532,846 B2 | 1/2017 | Nakamura |
| 9,532,849 B2 | 1/2017 | Anderson et al. |
| 9,538,962 B1 | 1/2017 | Hannaford et al. |
| 9,545,233 B2 | 1/2017 | Sirpad |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen |
| 9,561,446 B2 | 2/2017 | Brecher |
| 9,565,415 B2 | 2/2017 | Zhang et al. |
| 9,572,661 B2 | 2/2017 | Robin |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,629,595 B2 | 4/2017 | Walker |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque |
| 9,684,980 B2 | 6/2017 | Royalty et al. |
| 9,690,119 B2 | 6/2017 | Garofolo et al. |
| RE46,463 E | 7/2017 | Feinbloom |
| 9,693,748 B2 | 7/2017 | Rai et al. |
| 9,710,968 B2 | 7/2017 | Dillavou et al. |
| 9,713,502 B2 | 7/2017 | Finkman |
| 9,724,119 B2 | 8/2017 | Hissong |
| 9,724,165 B2 | 8/2017 | Arata et al. |
| 9,726,888 B2 | 8/2017 | Giartisio |
| 9,728,006 B2 | 8/2017 | Varga |
| 9,729,831 B2 | 8/2017 | Birnkrant |
| 9,757,034 B2 | 9/2017 | Desjardins |
| 9,757,087 B2 | 9/2017 | Simon et al. |
| 9,766,441 B2 | 9/2017 | Rappel |
| 9,767,608 B2 | 9/2017 | Lee et al. |
| 9,770,203 B1 | 9/2017 | Berme |
| 9,772,102 B1 | 9/2017 | Ferguson |
| 9,772,495 B2 | 9/2017 | Tam |
| 9,791,138 B1 | 10/2017 | Feinbloom |
| 9,800,995 B2 | 10/2017 | Libin |
| 9,805,504 B2 | 10/2017 | Zhang |
| 9,808,148 B2 | 11/2017 | Miller |
| 9,839,448 B2 | 12/2017 | Reckling et al. |
| 9,844,413 B2 | 12/2017 | Daon et al. |
| 9,851,080 B2 | 12/2017 | Wilt |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |
| 9,886,760 B2 | 2/2018 | Liu et al. |
| 9,892,564 B1 | 2/2018 | Cvetko et al. |
| 9,898,866 B2 | 2/2018 | Fuchs et al. |
| 9,901,414 B2 | 2/2018 | Lively |
| 9,911,187 B2 | 3/2018 | Steinle |
| 9,927,611 B2 | 3/2018 | Rudy |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,952,664 B2 | 4/2018 | Border et al. |
| 9,956,054 B2 | 5/2018 | Aguirre-Valencia |
| 9,958,674 B2 | 5/2018 | Border |
| 9,959,620 B2 | 5/2018 | Merlet |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Ben-Yishai et al. |
| 10,022,104 B2 | 7/2018 | Sell et al. |
| 10,023,615 B2 | 7/2018 | Bonny |
| 10,026,015 B2 | 7/2018 | Cavusoglu |
| 10,034,713 B2 | 7/2018 | Yang et al. |
| 10,046,165 B2 | 8/2018 | Frewin |
| 10,055,838 B2 | 8/2018 | Elenbaas et al. |
| 10,066,816 B2 | 9/2018 | Chang |
| 10,067,359 B1 | 9/2018 | Ushakov |
| 10,073,515 B2 | 9/2018 | Awdeh |
| 10,080,616 B2 | 9/2018 | Wilkinson et al. |
| 10,082,680 B2 | 9/2018 | Chang |
| 10,085,709 B2 | 10/2018 | Lavallee et al. |
| 10,105,187 B2 | 10/2018 | Corndorf et al. |
| 10,107,483 B2 | 10/2018 | Oren |

(56) References Cited

U.S. PATENT DOCUMENTS

| | | |
|---|---|---|
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom |
| 10,134,166 B2 | 11/2018 | Benishti et al. |
| 10,134,194 B2 | 11/2018 | Kepner |
| 10,139,652 B2 | 11/2018 | Windham |
| 10,139,920 B2 | 11/2018 | Isaacs |
| 10,142,496 B1 | 11/2018 | Rao |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman |
| 10,207,315 B2 | 2/2019 | Appleby |
| 10,212,517 B1 | 2/2019 | Beltran et al. |
| 10,230,719 B2 | 3/2019 | Vaugn |
| 10,231,893 B2 | 3/2019 | Lei |
| 10,235,606 B2 | 3/2019 | Miao |
| 10,240,769 B1 | 3/2019 | Braganca |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca |
| 10,357,146 B2 | 7/2019 | Fiebel |
| 10,357,574 B2 | 7/2019 | Hilderbrand |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Shousha |
| 10,398,514 B2 | 9/2019 | Ryan et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat |
| 10,433,814 B2 | 10/2019 | Razzaque |
| 10,434,335 B2 | 10/2019 | Takahashi |
| 10,441,236 B2 | 10/2019 | Bar-Tal et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski |
| 10,453,187 B2 | 10/2019 | Peterson |
| 10,463,434 B2 | 11/2019 | Siegler et al. |
| 10,465,892 B1 | 11/2019 | Feinbloom |
| 10,466,487 B2 | 11/2019 | Blum et al. |
| 10,470,732 B2 | 11/2019 | Baumgart |
| 10,473,314 B1 | 11/2019 | Braganca |
| 10,485,989 B2 | 11/2019 | Jordan |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 | 12/2019 | Edwards et al. |
| 10,504,231 B2 | 12/2019 | Fiala |
| 10,507,066 B2 | 12/2019 | DiMaio |
| 10,511,822 B2 | 12/2019 | Casas |
| 10,517,544 B2 | 12/2019 | Taguchi |
| 10,537,395 B2 | 1/2020 | Perez |
| 10,540,780 B1 | 1/2020 | Cousins |
| 10,543,485 B2 | 1/2020 | Ismagilov |
| 10,546,423 B2 | 1/2020 | Jones et al. |
| 10,548,557 B2 | 2/2020 | Lim |
| 10,555,775 B2 | 2/2020 | Hoffman |
| 10,568,535 B2 | 2/2020 | Roberts et al. |
| 10,571,696 B2 | 2/2020 | Urey et al. |
| 10,571,716 B2 | 2/2020 | Chapiro |
| 10,573,087 B2 | 2/2020 | Gallop et al. |
| 10,602,114 B2 | 2/2020 | Casas |
| 10,577,630 B2 | 3/2020 | Zhang |
| 10,586,400 B2 | 3/2020 | Douglas |
| 10,591,737 B2 | 3/2020 | Yildiz et al. |
| 10,592,748 B1 | 3/2020 | Cousins |
| 10,595,716 B2 | 3/2020 | Nazareth |
| 10,601,950 B2 | 3/2020 | Devam et al. |
| 10,603,113 B2 | 3/2020 | Lang |
| 10,603,133 B2 | 3/2020 | Wang et al. |
| 10,606,085 B2 | 3/2020 | Toyama |
| 10,594,998 B1 | 4/2020 | Casas |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi |
| 10,626,473 B2 | 4/2020 | Mariani |
| 10,631,905 B2 | 4/2020 | Asfora et al. |
| 10,631,907 B2 | 4/2020 | Zucker |
| 10,634,331 B1 | 4/2020 | Feinbloom |
| 10,634,921 B2 | 4/2020 | Blum et al. |
| 10,638,080 B2 | 4/2020 | Ovchinnikov |
| 10,646,285 B2 | 5/2020 | Siemionow et al. |
| 10,650,513 B2 | 5/2020 | Penney et al. |
| 10,650,594 B2 | 5/2020 | Jones |
| 10,652,525 B2 | 5/2020 | Woods |
| 10,653,495 B2 | 5/2020 | Gregerson et al. |
| 10,660,715 B2 | 5/2020 | Dozeman |
| 10,663,738 B2 | 5/2020 | Carlvik |
| 10,672,145 B2 | 6/2020 | Albiol et al. |
| 10,682,112 B2 | 6/2020 | Pizaine |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori |
| 10,706,540 B2 | 7/2020 | Merlet |
| 10,709,398 B2 | 7/2020 | Schweizer |
| 10,713,801 B2 | 7/2020 | Jordan |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,743,943 B2 | 8/2020 | Razeto et al. |
| 10,747,315 B2 | 8/2020 | Tungare |
| 10,748,319 B1 | 8/2020 | Tao et al. |
| 10,758,315 B2 | 9/2020 | Johnson et al. |
| 10,777,094 B1 | 9/2020 | Rao |
| 10,777,315 B2 | 9/2020 | Zehavi |
| 10,781,482 B2 | 9/2020 | Gubatayao |
| 10,792,110 B2 | 10/2020 | Leung et al. |
| 10,799,145 B2 | 10/2020 | West et al. |

(56) References Cited

U.S. PATENT DOCUMENTS

| | | |
|---|---|---|
| 10,799,296 B2 | 10/2020 | Lang |
| 10,799,298 B2 | 10/2020 | Crawford et al. |
| 10,799,316 B2 | 10/2020 | Sela et al. |
| 10,810,799 B2 | 10/2020 | Tepper et al. |
| 10,818,019 B2 | 10/2020 | Piat |
| 10,818,101 B2 | 10/2020 | Gallop et al. |
| 10,818,199 B2 | 10/2020 | Buras et al. |
| 10,825,563 B2 | 11/2020 | Gibby et al. |
| 10,831,943 B2 | 11/2020 | Santarone |
| 10,835,296 B2 | 11/2020 | Elimelech |
| 10,838,206 B2 | 11/2020 | Fortin-Deschenes et al. |
| 10,839,629 B2 | 11/2020 | Jones |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino |
| 10,869,517 B1 | 12/2020 | Halpern |
| 10,869,727 B2 | 12/2020 | Yanof et al. |
| 10,872,472 B2 | 12/2020 | Watola |
| 10,877,262 B1 | 12/2020 | Luxembourg |
| 10,877,296 B2 | 12/2020 | Lindsey |
| 10,878,639 B2 | 12/2020 | Douglas et al. |
| 10,893,260 B2 | 1/2021 | Trail et al. |
| 10,895,742 B2 | 1/2021 | Schneider |
| 10,895,743 B2 | 1/2021 | Dausmann |
| 10,895,906 B2 | 1/2021 | West et al. |
| 10,898,151 B2 | 1/2021 | Harding et al. |
| 10,921,595 B2 | 2/2021 | Rakshit |
| 10,921,613 B2 | 2/2021 | Gupta et al. |
| 10,928,321 B2 | 2/2021 | Rawle |
| 10,928,638 B2 | 2/2021 | Ninan |
| 10,929,670 B1 | 2/2021 | Troy et al. |
| 10,935,815 B1 | 3/2021 | Castaneda |
| 10,935,816 B2 | 3/2021 | Ban |
| 10,936,537 B2 | 3/2021 | Huston |
| 10,939,973 B2 | 3/2021 | DiMaio |
| 10,939,977 B2 | 3/2021 | Messinger et al. |
| 10,941,933 B2 | 3/2021 | Ferguson |
| 10,946,108 B2 | 3/2021 | Zhang |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,993,754 B2 | 5/2021 | Kuntz et al. |
| 11,000,335 B2 | 5/2021 | Dorman |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti |
| 11,013,573 B2 | 5/2021 | Chang |
| 11,013,900 B2 | 5/2021 | Malek |
| 11,019,988 B2 | 6/2021 | Fiebel |
| 11,027,027 B2 | 6/2021 | Manning |
| 11,029,147 B2 | 6/2021 | Abovitz et al. |
| 11,030,809 B2 | 6/2021 | Wang |
| 11,041,173 B2 | 6/2021 | Zhang |
| 11,045,663 B2 | 6/2021 | Mori |
| 11,049,293 B2 | 6/2021 | Chae |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,064,904 B2 | 7/2021 | Kay et al. |
| 11,065,062 B2 | 7/2021 | Frushour |
| 11,067,387 B2 | 7/2021 | Marell |
| 11,071,497 B2 | 7/2021 | Hallack |
| 11,079,596 B2 | 8/2021 | Hua et al. |
| 11,087,039 B2 | 8/2021 | Duff |
| 11,090,019 B2 | 8/2021 | Siemionow et al. |
| 11,097,129 B2 | 8/2021 | Sakata |
| 11,099,376 B1 | 8/2021 | Steier |
| 11,103,320 B2 | 8/2021 | LeBoeuf |
| D930,162 S | 9/2021 | Cremer et al. |
| 11,109,762 B1 | 9/2021 | Steier |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford |
| 11,135,016 B2 | 10/2021 | Frielinghaus et al. |
| 11,137,610 B1 | 10/2021 | Kessler et al. |
| 11,141,221 B2 | 10/2021 | Hobeika |
| 11,153,549 B2 | 10/2021 | Casas |
| 11,153,555 B1 | 11/2021 | Healy et al. |
| 11,163,176 B2 | 11/2021 | Karafin |
| 11,164,324 B2 | 11/2021 | Liu |
| 11,166,006 B2 | 11/2021 | Hegyi |
| 11,172,990 B2 | 11/2021 | Lang |
| 11,179,136 B2 | 11/2021 | Kohli |
| 11,180,557 B2 | 11/2021 | Noelle |
| 11,181,747 B1 | 11/2021 | Kessler et al. |
| 11,185,891 B2 | 11/2021 | Cousins |
| 11,202,682 B2 | 12/2021 | Staunton |
| 11,207,150 B2 | 12/2021 | Healy |
| 11,217,028 B2 | 1/2022 | Jones |
| 11,224,483 B2 | 1/2022 | Steinberg et al. |
| 11,224,763 B2 | 1/2022 | Takahashi |
| 11,227,417 B2 | 1/2022 | Berlinger |
| 11,231,787 B2 | 1/2022 | Isaacs et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao |
| 11,257,241 B2 | 2/2022 | Tao |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt |
| 11,284,846 B2 | 3/2022 | Graumann |
| 11,311,341 B2 | 3/2022 | Lang |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,621 B2 | 4/2022 | Merschon et al. |
| 11,304,759 B2 | 4/2022 | Kovtun et al. |
| 11,307,402 B2 | 4/2022 | Steier |
| 11,308,663 B2 | 4/2022 | Alhrishy et al. |
| 11,317,973 B2 | 5/2022 | Calloway |
| 11,337,763 B2 | 5/2022 | Choi |
| 11,348,257 B2 | 5/2022 | Lang |
| 11,350,072 B1 | 5/2022 | Casas |
| 11,350,965 B2 | 6/2022 | Yilmaz et al. |
| 11,351,006 B2 | 6/2022 | Aferzon |
| 11,354,813 B2 | 6/2022 | Piat et al. |
| 11,360,315 B2 | 6/2022 | Tu |
| 11,382,699 B2 | 7/2022 | Wassall |
| 11,382,700 B2 | 7/2022 | Calloway |
| 11,382,712 B2 | 7/2022 | Elimelech et al. |
| 11,382,713 B2 | 7/2022 | Healy |
| 11,389,252 B2 | 7/2022 | Gera et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,423,554 B2 | 8/2022 | Borsdorf et al. |
| 11,432,828 B1 | 9/2022 | Lang |
| 11,432,931 B2 | 9/2022 | Lang |
| 11,452,568 B2 | 9/2022 | Lang |
| 11,460,915 B2 | 10/2022 | Frielinghaus |
| 11,461,983 B2 | 10/2022 | Jones |
| 11,464,581 B2 | 10/2022 | Calloway |
| 11,478,214 B2 | 10/2022 | Siewerdsen et al. |
| 11,483,532 B2 | 10/2022 | Casas |

(56) References Cited

U.S. PATENT DOCUMENTS

| | | |
|---|---|---|
| 11,490,986 B2 | 11/2022 | Ben-Yishai |
| 11,527,002 B2 | 12/2022 | Govari |
| 11,528,393 B2 | 12/2022 | Garofolo et al. |
| 11,627,924 B2 | 4/2023 | Alexandroni et al. |
| 11,648,016 B2 | 5/2023 | Hathaway et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,712,582 B2 | 8/2023 | Miyazaki et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,826,111 B2 | 11/2023 | Mahfouz |
| 11,839,501 B2 | 12/2023 | Takahashi et al. |
| 11,885,752 B2 | 1/2024 | St-Aubin et al. |
| 11,896,445 B2 | 2/2024 | Gera et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |
| 2004/0138556 A1 | 7/2004 | Cosman |
| 2005/0017972 A1 | 1/2005 | Poole et al. |
| 2005/0024586 A1 | 2/2005 | Teiwes et al. |
| 2005/0119639 A1 | 6/2005 | McCombs et al. |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2005/0267358 A1* | 12/2005 | Tuma .................. A61B 90/39 600/414 |
| 2006/0072124 A1 | 4/2006 | Smetak et al. |
| 2006/0134198 A1 | 6/2006 | Tawa |
| 2006/0176242 A1 | 8/2006 | Jaramaz et al. |
| 2007/0018975 A1 | 1/2007 | Chuanggui et al. |
| 2007/0058261 A1 | 3/2007 | Sugihara et al. |
| 2007/0100325 A1 | 5/2007 | Jutras et al. |
| 2007/0233371 A1 | 10/2007 | Stoschek et al. |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0018437 A1 | 1/2009 | Cooke |
| 2009/0024127 A1 | 1/2009 | Lechner et al. |
| 2009/0062869 A1 | 3/2009 | Claverie et al. |
| 2009/0099445 A1 | 4/2009 | Burger |
| 2009/0036902 A1 | 5/2009 | Dimaio et al. |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0216060 A1 | 9/2011 | Weising et al. |
| 2011/0245625 A1 | 10/2011 | Trovato et al. |
| 2011/0254922 A1 | 10/2011 | Schaerer et al. |
| 2011/0306873 A1 | 12/2011 | Shenai et al. |
| 2012/0014608 A1 | 1/2012 | Watanabe et al. |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1 | 9/2012 | Healy et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0079829 A1 | 3/2013 | Globerman et al. |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao |
| 2013/0195338 A1 | 8/2013 | Xu et al. |
| 2013/0209953 A1 | 8/2013 | Arlinsky et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1 | 9/2013 | Maier-Hein et al. |
| 2013/0249787 A1 | 9/2013 | Morimota |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278635 A1 | 10/2013 | Maggiore |
| 2013/0300760 A1 | 11/2013 | Sugano et al. |
| 2013/0342571 A1 | 12/2013 | Kinnebrew et al. |
| 2014/0031668 A1 | 1/2014 | Mobasser et al. |
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2014/0361956 A1 | 12/2014 | Mikhailov et al. |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Labor |
| 2015/0150641 A1 | 6/2015 | Daon et al. |
| 2015/0182293 A1 | 7/2015 | Yang et al. |

(56) References Cited

U.S. PATENT DOCUMENTS

| | | |
|---|---|---|
| 2015/0209119 A1 | 7/2015 | Theodore et al. |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit et al. |
| 2015/0287236 A1 | 10/2015 | Winn |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0338652 A1 | 11/2015 | Lim et al. |
| 2015/0338653 A1 | 11/2015 | Subramaniam et al. |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0015878 A1 | 1/2016 | Graham et al. |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang |
| 2016/0163045 A1 | 6/2016 | Penney et al. |
| 2016/0175064 A1 | 6/2016 | Stenile et al. |
| 2016/0178910 A1 | 6/2016 | Gudicell et al. |
| 2016/0191887 A1 | 6/2016 | Casas |
| 2016/0223822 A1 | 8/2016 | Harrison et al. |
| 2016/0246059 A1 | 8/2016 | Halpin et al. |
| 2016/0249989 A1 | 9/2016 | Devam et al. |
| 2016/0256223 A1 | 9/2016 | Haimer et al. |
| 2016/0275684 A1 | 9/2016 | Elenbaas et al. |
| 2016/0302870 A1 | 10/2016 | Wilkinson et al. |
| 2016/0324580 A1 | 11/2016 | Esterberg |
| 2016/0324583 A1 | 11/2016 | Kheradpr et al. |
| 2016/0339337 A1 | 11/2016 | Ellsworth et al. |
| 2017/0024634 A1 | 1/2017 | Miao et al. |
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1 | 2/2017 | Greenhalgh et al. |
| 2017/0068119 A1 | 3/2017 | Antaki |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0014119 A1 | 6/2017 | Capote et al. |
| 2017/0164919 A1 | 6/2017 | LaVallee et al. |
| 2017/0164920 A1 | 6/2017 | Lavallee et al. |
| 2017/0178375 A1 | 6/2017 | Benishti et al. |
| 2017/0220224 A1 | 8/2017 | Kodali |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penne |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0117150 A1 | 5/2018 | O'Dwyer |
| 2018/0133871 A1 | 5/2018 | Farmer |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1 | 7/2018 | Gregerson et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0311011 A1 | 11/2018 | Van Beek et al. |
| 2018/0317803 A1 | 11/2018 | Ben-Yishai et al. |
| 2018/0318035 A1 | 11/2018 | McLachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper |
| 2019/0043238 A1 | 2/2019 | Benishti et al. |
| 2019/0043392 A1 | 2/2019 | Abele |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1 | 4/2019 | Johnson et al. |
| 2019/0130792 A1 | 5/2019 | Rios |
| 2019/0142519 A1 | 5/2019 | Siemionow et al. |
| 2019/0144443 A1 | 5/2019 | Jackson |
| 2019/0175228 A1* | 6/2019 | Elimelech ............ A61B 17/122 |
| 2019/0192230 A1 | 6/2019 | Siemionow et al. |
| 2019/0201106 A1 | 7/2019 | Siemionow et al. |
| 2019/0216537 A1 | 7/2019 | Eltorai |
| 2019/0254753 A1 | 8/2019 | Johnson |
| 2019/0273916 A1 | 9/2019 | Benishti et al. |
| 2019/0310481 A1 | 10/2019 | Blum et al. |
| 2019/0333480 A1 | 10/2019 | Lang |
| 2019/0369660 A1 | 12/2019 | Wen et al. |
| 2019/0369717 A1 | 12/2019 | Frielinghaus |
| 2019/0387351 A1 | 12/2019 | Lyren |
| 2020/0019364 A1 | 1/2020 | Pond |
| 2020/0020249 A1 | 1/2020 | Jarc et al. |
| 2020/0038112 A1 | 2/2020 | Amanatullah et al. |
| 2020/0043160 A1 | 2/2020 | Mizukura et al. |
| 2020/0078100 A1 | 3/2020 | Weinstein et al. |
| 2020/0085511 A1 | 3/2020 | Oezbek et al. |
| 2020/0088997 A1 | 3/2020 | Lee |
| 2020/0159313 A1 | 3/2020 | Gibby et al. |
| 2020/0100847 A1 | 4/2020 | Siegler et al. |
| 2020/0117025 A1 | 4/2020 | Sauer |
| 2020/0129058 A1 | 4/2020 | Li |
| 2020/0129136 A1 | 4/2020 | Harding et al. |
| 2020/0129262 A1 | 4/2020 | Verard |
| 2020/0129264 A1 | 4/2020 | Onativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene |
| 2020/0151507 A1 | 5/2020 | Siemionow et al. |
| 2020/0156259 A1 | 5/2020 | Morales |
| 2020/0163723 A1 | 5/2020 | Wolf et al. |
| 2020/0163739 A1 | 5/2020 | Messinger et al. |
| 2020/0184638 A1 | 6/2020 | Meglan |
| 2020/0186786 A1 | 6/2020 | Gibby et al. |
| 2020/0188028 A1 | 6/2020 | Feiner et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent |
| 2020/0242280 A1 | 7/2020 | Pavloff et al. |

(56) References Cited

U.S. PATENT DOCUMENTS

| | | |
|---|---|---|
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei |
| 2020/0275988 A1 | 9/2020 | Johnson |
| 2020/0281554 A1 | 9/2020 | Trini et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler |
| 2020/0341283 A1 | 10/2020 | McCracken |
| 2020/0352655 A1 | 11/2020 | Freese |
| 2020/0355927 A1 | 11/2020 | Marcellin-Dibon |
| 2020/0360091 A1 | 11/2020 | Murray et al. |
| 2020/0288075 A1 | 12/2020 | Kazanzides et al. |
| 2020/0375666 A1 | 12/2020 | Murphy |
| 2020/0377493 A1 | 12/2020 | Heiser |
| 2020/0377956 A1 | 12/2020 | Vogelstein |
| 2020/0388075 A1 | 12/2020 | Kazanzides et al. |
| 2020/0389425 A1 | 12/2020 | Bhatia |
| 2020/0390502 A1 | 12/2020 | Holthuizen et al. |
| 2020/0390503 A1 | 12/2020 | Casas et al. |
| 2020/0402647 A1 | 12/2020 | Domracheva et al. |
| 2020/0409306 A1 | 12/2020 | Gelman et al. |
| 2020/0410687 A1 | 12/2020 | Siemionow et al. |
| 2020/0413031 A1 | 12/2020 | Khani |
| 2021/0004956 A1 | 1/2021 | Book et al. |
| 2021/0009339 A1 | 1/2021 | Morrison et al. |
| 2021/0015560 A1 | 1/2021 | Boddington et al. |
| 2021/0015583 A1 | 1/2021 | Avisar |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi et al. |
| 2021/0030511 A1 | 2/2021 | Wolf et al. |
| 2021/0038339 A1 | 2/2021 | Yu |
| 2021/0049825 A1 | 2/2021 | Wheelwright et al. |
| 2021/0052348 A1 | 2/2021 | Stifter et al. |
| 2021/0065911 A1 | 3/2021 | Goel et al. |
| 2021/0077195 A1 | 3/2021 | Saeidi |
| 2021/0077210 A1 | 3/2021 | Itkowitz |
| 2021/0080751 A1 | 3/2021 | Lindsey |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quid et al. |
| 2021/0093417 A1 | 4/2021 | Liu |
| 2021/0104055 A1 | 4/2021 | Ni et al. |
| 2021/0107923 A1 | 4/2021 | Jackson |
| 2021/0109349 A1 | 4/2021 | Schneider |
| 2021/0109373 A1 | 4/2021 | Loo |
| 2021/0110517 A1 | 4/2021 | Flohr |
| 2021/0113269 A1 | 4/2021 | Vilsmeier |
| 2021/0113293 A9 | 4/2021 | Silva et al. |
| 2021/0121238 A1 | 4/2021 | Palushi et al. |
| 2021/0137634 A1 | 5/2021 | Lang et al. |
| 2021/0141887 A1 | 5/2021 | Kim et al. |
| 2021/0150702 A1 | 5/2021 | Claessen et al. |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1 | 7/2021 | Bristol et al. |
| 2021/0223577 A1 | 7/2021 | Zheng |
| 2021/0227791 A1 | 7/2021 | De Oliveira Seixas |
| 2021/0231301 A1 | 7/2021 | Hikmet et al. |
| 2021/0235061 A1 | 7/2021 | Hegyi |
| 2021/0248822 A1 | 8/2021 | Choi |
| 2021/0278675 A1 | 9/2021 | Klug et al. |
| 2021/0282887 A1 | 9/2021 | Wiggermann |
| 2021/0290046 A1 | 9/2021 | Nazareth |
| 2021/0290336 A1 | 9/2021 | Wang |
| 2021/0290394 A1 | 9/2021 | Mahfouz |
| 2021/0295512 A1 | 9/2021 | Knoplioch et al. |
| 2021/0298835 A1 | 9/2021 | Wang |
| 2021/0306599 A1 | 9/2021 | Pierce |
| 2021/0311322 A1 | 10/2021 | Belanger |
| 2021/0314502 A1 | 10/2021 | Liu |
| 2021/0315636 A1 | 10/2021 | Akbarian |
| 2021/0315662 A1 | 10/2021 | Freeman et al. |
| 2021/0325684 A1 | 10/2021 | Ninan |
| 2021/0333561 A1 | 10/2021 | Oh |
| 2021/0341739 A1 | 11/2021 | Cakmakci et al. |
| 2021/0341740 A1 | 11/2021 | Cakmakci et al. |
| 2021/0346115 A1 | 11/2021 | Dulin et al. |
| 2021/0349677 A1 | 11/2021 | Baldev |
| 2021/0364802 A1 | 11/2021 | Uchiyama et al. |
| 2021/0369226 A1 | 12/2021 | Siemionow et al. |
| 2021/0371413 A1 | 12/2021 | Thurston |
| 2021/0373333 A1 | 12/2021 | Moon |
| 2021/0373344 A1 | 12/2021 | Loyola |
| 2021/0378757 A1 | 12/2021 | Bay |
| 2021/0386482 A1 | 12/2021 | Gera et al. |
| 2021/0389590 A1 | 12/2021 | Freeman |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0071712 A1 | 3/2022 | Wolf et al. |
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0142730 A1 | 5/2022 | Wolf et al. |
| 2022/0155861 A1 | 5/2022 | Myung |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |
| 2022/0269077 A1 | 8/2022 | Adema et al. |
| 2022/0270263 A1 | 8/2022 | Junio |
| 2022/0133484 A1 | 9/2022 | Lang |
| 2022/0287676 A1 | 9/2022 | Steines et al. |
| 2022/0295033 A1 | 9/2022 | Casas |
| 2022/0304768 A1 | 9/2022 | Elimelech et al. |
| 2022/0351385 A1 | 11/2022 | Finley et al. |
| 2022/0358759 A1 | 11/2022 | Cork et al. |
| 2022/0392085 A1 | 12/2022 | Finley et al. |
| 2022/0405935 A1 | 12/2022 | Flossmann et al. |
| 2023/0009793 A1 | 1/2023 | Gera et al. |
| 2023/0027801 A1 | 1/2023 | Qian et al. |
| 2023/0073041 A1 | 3/2023 | Samadani et al. |
| 2023/0149083 A1 | 5/2023 | Lin et al. |
| 2023/0290037 A1 | 9/2023 | Tasse et al. |
| 2023/0295302 A1 | 9/2023 | Bhagavatheeswaran et al. |
| 2023/0316550 A1 | 10/2023 | Hiasa |
| 2023/0329799 A1 | 10/2023 | Gera et al. |

(56) References Cited

U.S. PATENT DOCUMENTS

| | | |
|---|---|---|
| 2023/0329801 A1 | 10/2023 | Elimelech et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386153 A1 | 11/2023 | Rybnikov et al. |
| 2023/0397349 A1 | 12/2023 | Capelli et al. |
| 2023/0397957 A1 | 12/2023 | Crawford et al. |
| 2023/0410445 A1 | 12/2023 | Elimelech et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |
| 2024/0041558 A1 | 2/2024 | Siewerdsen et al. |
| 2024/0126087 A1 | 4/2024 | Gera et al. |
| 2024/0127559 A1 | 4/2024 | Rybnikov et al. |
| 2024/0130826 A1 | 4/2024 | Elimelech et al. |
| 2024/0134206 A1 | 4/2024 | Gera et al. |

FOREIGN PATENT DOCUMENTS

| | | |
|---|---|---|
| CN | 101379412 B | 3/2009 |
| CN | 103106348 A | 5/2013 |
| CN | 111915696 A | 11/2020 |
| CN | 112489047 B | 3/2021 |
| DE | 202004011567 U1 | 11/2004 |
| DE | 102004011567 A1 | 9/2005 |
| DE | 102014008153 A1 | 10/2014 |
| DE | 202022103168 U1 | 6/2022 |
| EP | 0933096 A2 | 8/1999 |
| EP | 1640750 A1 | 3/2006 |
| EP | 1757974 A1 | 2/2007 |
| EP | 2119397 A1 | 11/2009 |
| EP | 2557998 A1 | 2/2013 |
| EP | 2823463 A1 | 1/2015 |
| EP | 2868277 A1 | 5/2015 |
| EP | 2134847 B1 | 6/2015 |
| EP | 2963616 A2 | 1/2016 |
| EP | 3028258 A1 | 6/2016 |
| EP | 3037038 A1 | 6/2016 |
| EP | 3069318 A1 | 9/2016 |
| EP | 2891966 B1 | 1/2017 |
| EP | 3121789 A1 | 1/2017 |
| EP | 3123970 A1 | 2/2017 |
| EP | 2654749 B1 | 5/2017 |
| EP | 3175815 A1 | 6/2017 |
| EP | 3216416 A1 | 9/2017 |
| EP | 2032039 B1 | 10/2017 |
| EP | 3247297 A1 | 11/2017 |
| EP | 3256213 A1 | 12/2017 |
| EP | 3306567 A1 | 4/2018 |
| EP | 3320874 A1 | 5/2018 |
| EP | 2030193 B1 | 7/2018 |
| EP | 2225723 B1 | 2/2019 |
| EP | 3034607 B1 | 3/2019 |
| EP | 2892558 B1 | 4/2019 |
| EP | 2635299 B1 | 7/2019 |
| EP | 3505050 A1 | 7/2019 |
| EP | 3224376 B1 | 8/2019 |
| EP | 2875149 B1 | 12/2019 |
| EP | 3206583 B1 | 9/2020 |
| EP | 3711700 A1 | 9/2020 |
| EP | 2625845 B1 | 3/2021 |
| EP | 3076660 B1 | 4/2021 |
| EP | 3858280 A1 | 8/2021 |
| EP | 3593227 B1 | 9/2021 |
| EP | 3913423 A1 | 11/2021 |
| EP | 3789965 B1 | 12/2021 |
| EP | 3634294 B1 | 1/2022 |
| EP | 3952331 A1 | 2/2022 |
| EP | 3960235 A1 | 3/2022 |
| EP | 4173590 A1 | 5/2023 |
| EP | 4252695 A1 | 10/2023 |
| EP | 4270313 A1 | 11/2023 |
| EP | 4287120 A1 | 12/2023 |
| GB | 2507314 A | 4/2014 |
| JP | 2009-514571 A | 4/2009 |
| JP | 2021-525186 A | 9/2021 |
| KR | 20140120155 A | 10/2014 |
| WO | 03034705 A2 | 4/2003 |
| WO | 2007051304 A1 | 5/2007 |
| WO | 2007115826 A2 | 10/2007 |
| WO | 2008103383 A1 | 8/2008 |
| WO | 2010067267 A1 | 6/2010 |
| WO | WO2010074747 A1 | 7/2010 |
| WO | WO2012101286 A1 | 8/2012 |
| WO | 2013112554 A1 | 8/2013 |
| WO | 2014024188 A1 | 2/2014 |
| WO | 2014037953 A2 | 3/2014 |
| WO | 2014113455 A1 | 7/2014 |
| WO | 2014125789 A1 | 8/2014 |
| WO | 2014167563 A1 | 10/2014 |
| WO | 2014174067 A1 | 10/2014 |
| WO | 2015058816 A1 | 4/2015 |
| WO | WO2015061752 A1 | 4/2015 |
| WO | WO2015109145 A1 | 7/2015 |
| WO | 2016151506 A1 | 9/2016 |
| WO | 2018/052966 A1 | 3/2018 |
| WO | 2018073452 A1 | 4/2018 |
| WO | WO2018200767 A1 | 4/2018 |
| WO | 2018206086 A1 | 11/2018 |
| WO | 2019/083431 A1 | 5/2019 |
| WO | 2019/135209 A1 | 7/2019 |
| WO | 2019/161477 A1 | 8/2019 |
| WO | 2019195926 A1 | 10/2019 |
| WO | 2019211741 A1 | 11/2019 |
| WO | WO2019210353 A1 | 11/2019 |
| WO | 2020109903 A1 | 6/2020 |
| WO | 2020109904 A1 | 6/2020 |
| WO | 2021019369 A1 | 2/2021 |
| WO | WO2021017019 A1 | 2/2021 |
| WO | WO2021023574 A1 | 2/2021 |
| WO | WO2021046455 A1 | 3/2021 |
| WO | WO2021048158 A1 | 3/2021 |
| WO | WO2021021979 A2 | 4/2021 |
| WO | WO2021061459 A1 | 4/2021 |
| WO | WO2021062375 A1 | 4/2021 |
| WO | WO2021073743 A1 | 4/2021 |
| WO | WO2021087439 A1 | 5/2021 |
| WO | WO2021091980 A1 | 5/2021 |
| WO | 2021255627 A1 | 6/2021 |
| WO | WO2021112918 A1 | 6/2021 |
| WO | 2021130564 A1 | 7/2021 |
| WO | WO2021137752 A1 | 7/2021 |
| WO | WO2021141887 A1 | 7/2021 |
| WO | WO2021145584 A1 | 7/2021 |
| WO | WO2021154076 A1 | 8/2021 |
| WO | 2021/188757 A1 | 9/2021 |
| WO | WO2021183318 A2 | 12/2021 |
| WO | WO2021257897 A1 | 12/2021 |
| WO | WO2021258078 A1 | 12/2021 |
| WO | WO2022009233 A1 | 1/2022 |
| WO | 2022053923 A1 | 3/2022 |
| WO | 2022079565 A1 | 4/2022 |
| WO | 2023281395 A1 | 1/2023 |
| WO | 2023/011924 A1 | 2/2023 |
| WO | 2023007418 A1 | 2/2023 |
| WO | 2023021448 A1 | 2/2023 |
| WO | 2023021450 A1 | 2/2023 |
| WO | 2023021451 A1 | 2/2023 |
| WO | 2023/047355 A1 | 3/2023 |
| WO | 2023026229 A1 | 3/2023 |
| WO | 2023/072887 A1 | 5/2023 |
| WO | 2023/088986 A1 | 5/2023 |
| WO | 2023/163933 A1 | 8/2023 |
| WO | 2023/186996 A1 | 10/2023 |
| WO | 2023/205212 A1 | 10/2023 |
| WO | 2023/209014 A1 | 11/2023 |

(56) References Cited

FOREIGN PATENT DOCUMENTS

| WO | 2023/232492 A1 | 12/2023 |
|---|---|---|
| WO | 2023/240912 A1 | 12/2023 |
| WO | 2024/013642 A2 | 1/2024 |
| WO | 2024/018368 A2 | 1/2024 |

OTHER PUBLICATIONS

CN Application # 2019800757525 Office Action dated Mar. 1, 2022.
U.S. Appl. No. 16/200,144 Office Action dated Mar. 15, 2022.
U.S. Appl. No. 16/524,258 Office Action dated Apr. 11, 2022.
EP Application # 16767845.7 Office Action dated Apr. 29, 2022.
U.S. Appl. No. 16/419,023 Office Action dated Mar. 1, 2022.
Lorensen et al., "Marching Cubes: A High Resolution 3D Surface Construction Algorithm," ACM SIGGRAPH '87, Computer Graphics, vol. 21, No. 4, pp. 163-169, Jul. 1987.
Wikipedia, "Marching Cubes," pp. 1-4, last edited Sep. 4, 2021.
Milletari et al., "V-Net: fully Convolutional Neural Networks for Volumetric Medical Image Segmentation," arXiv:1606.04797v1, pp. 1-11, Jun. 15, 2016.
Webster (ed.), "Structured Light Techniques and Applications," Wiley Encyclopedia of Electrical and Electronics Engineering, pp. 1-24, year 2016.
Liberadzki et al., "Structured-Light-Based System for Shape Measurement of the Human Body in Motion," Sensors, vol. 18, pp. 1-19, year 2018.
Romero, "Volume Ray Casting Techniques and Applications Using General Purpose Computations on Graphics Processing Units," Thesis/Dissertation Collections, Rochester Institute of Technology, RIT Scholar Works, pp. 1-140, Jun. 2009.
Zhang et al., "Medical Volume Rendering Techniques," Independent Research, Spring 2014, arXiv:1802.07710v1, pp. 1-33, Feb. 21, 2018.
Van Ooijen et al., "Noninvasive Coronary Imaging Using Electron Beam CT: Surface Rendering Versus Volume Rendering," Computers in Radiology, AJR, vol. 180, pp. 223-226, Jan. 2003.
16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.
Everysight, Installing your RX Adaptor, accessed Mar. 13, 2024 at https://support.everysight.com/hc/en-us/articles/115000984571-Installing-your-RX-Adaptor.
Everysight, Raptor User Manual, copyright 2017, in 46 pages.
Frames Direct, InSpatialRx Prescription Insert, Prescription Insert for Magic Leap 1, accessed Mar. 8, 2024 at https://www.framesdirect.com/inspatialrx-prescription-insert.html.
Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Vuzix Blades, Prescription Lens Installation Guide, copyright 2020.
EP Application # 19891059.8 Search Report dated Jul. 27, 2022.
EP Application # 19890849.3 Search Report dated Jul. 27, 2022.
U.S. Appl. No. 16/419,023 Office Action dated Sep. 1, 2022.
U.S. Appl. No. 16/524,258 Office Action dated Oct. 24, 2022.
International Application PCT/IB2022/057965 Search Report dated Dec. 15, 2022.
U.S. Appl. No. 16/524,258 Office Action dated Jan. 24, 2023.
International Application PCT/IB2022/057733 Search Report dated Jan. 26, 2023.
European Application 22203956.2 Search Report dated Feb. 9, 2023.
International Application PCT/IB2022/059030 Search report dated Feb. 28, 2023.
U.S. Appl. No. 15/896,102 U.S. Pat. No. 10,134,166, filed Feb. 14, 2018 Nov. 20, 2018, Combining Video-Based and Optic-Based Augmented Reality in a Near Eye Display.
U.S. Appl. No. 16/159,740 U.S. Pat. No. 10/382,748, filed Oct. 15, 2018 Aug. 13, 2019, Combining Video-Based and Optic-Based Augmented Reality in a Near Eye Display.
U.S. Appl. No. 16/419,023, U.S. Pat. No. 11,750,794, filed May 22, 2019 Sep. 5, 2023, Combining Video-Based and Optic-Based Augmented Reality in a Near Eye Display.
U.S. Appl. No. 18/352,158, filed Jul. 13, 2023, Combining Video-Based and Optic-Based Augmented Reality in a Near Eye Display.
U.S. Appl. No. 18/365,643, filed Aug. 4, 2023, Head-Mounted Augmented Reality Near Eye Display Device.
U.S. Appl. No. 18/365,650, filed Aug. 4, 2023, Systems for Facilitating Augmented Reality-Assisted Medical Procedures.
U.S. Appl. No. 15/127,423 U.S. Pat. No. 9,928,629, filed Sep. 20, 2016 Mar. 27, 2018, Combining Video-Based and Optic-Based Augmented Reality in a Near Eye Display.
U.S. Appl. No. 16/120,480 U.S. Pat. No. 10,835,296, filed Sep. 4, 2018 Nov. 17, 2020, Spinous Process Clamp.
U.S. Appl. No. 17/067,831, filed Oct. 12, 2020, Spinous Process Clamp.
U.S. Appl. No. 18/030,072, filed Apr. 4, 2023, Spinous Process Clamp.
U.S. Appl. No. 18/365,590, filed Aug. 4, 2023, Registration of a Fiducial Marker for an Augmented Reality System.
U.S. Appl. No. 18/365,571 U.S. Pat. No. 11,974,887, filed Aug. 4, 2023 May 7, 2024, Registration Marker for an Augmented Reality System.
U.S. Appl. No. 18/632,588, filed Apr. 11, 2024, Registration of a Fiducial Marker for an Augmented Reality System.
U.S. Appl. No. 17/045,766, filed Oct. 7, 2020, Registration of a Fiducial Marker for an Augmented Reality System.
U.S. Appl. No. 16/199,281 U.S. Pat. No. 10,939,977, filed Nov. 26, 2018 Mar. 9, 2021, Positioning Marker.
U.S. Appl. No. 16/524,258, filed Jul. 29, 2019, Fiducial Marker.
U.S. Appl. No. 18/631,804, filed Apr. 10, 2024, Fiducial Marker.
U.S. Appl. No. 17/585,629, filed Jan. 27, 2022, Fiducial Marker.
U.S. Appl. No. 16/724,297 U.S. Pat. No. 11,382,712, filed Dec. 22, 2019 Jul. 2, 2022, Mirroring in Image Guided Surgery.
U.S. Appl. No. 17/827,710 U.S. Pat. No. 11,801,115, filed May 29, 2022 Oct. 31, 2023, Mirroring in Image Guided Surgery.
U.S. Appl. No. 18/352,181, filed Jul. 13, 2023, Mirroring in Image Guided Surgery.
U.S. Appl. No. 18/400,739, filed Dec. 29, 2023, Mirroring in Image Guided Surgery.
U.S. Appl. No. 16/200,144 U.S. Pat. No. 11,766,296, filed Nov. 26, 2018 Sep. 26, 2023, Tracking System for Image-Guided Surgery.
U.S. Appl. No. 18/470,809, filed Sep. 20, 2023, Tracking Methods for Image-Guided Surgery.
U.S. Appl. No. 18/631,877, filed Apr. 10, 2024, Tracking Systems and Methods for Image-Guided Surgery.
U.S. Appl. No. 17/015,199, filed Sep. 9, 2020, Universal Tool Adapter.
U.S. Appl. No. 18/598,965, filed Mar. 7, 2024, Universal Tool Adapter for Image Guided Surgery.
U.S. Appl. No. 18/044,380, filed Mar. 8, 2023, Universal Tool Adapter for Image Guided Surgery.
U.S. Appl. No. 16/901,026 U.S. Pat. No. 11,389,252, filed Jun. 15, 2020 Jul. 19, 2022, Rotating Marker for Image Guided Surgery.
U.S. Appl. No. 18/008,980, filed Dec. 8, 2022, Rotating Marker.
U.S. Appl. No. 17/368,859 U.S. Pat. No. 11,896,445, filed Jul. 7, 2021 Feb. 13, 2024, Iliac Pin and Adapter.
U.S. Appl. No. 18/437,898, filed Feb. 9, 2024, Iliac Pin and Adapter.
U.S. Appl. No. 18/576,516, filed Jan. 4, 2024, Iliac Pin and Adapter.
U.S. Appl. No. 18/291,731, filed Jan. 24, 2024, Rotating Marker and Adapter for Image-Guided Surgery.
U.S. Appl. No. 18/365,844, filed Aug. 4, 2023, Augmented-Reality Surgical System Using Depth Sensing.
U.S. Appl. No. 18/683,676, filed Feb. 14, 2024, Stereoscopic Display and Digital Loupe for Augmented-Reality Near-Eye Display.
U.S. Appl. No. 18/683,680, filed Feb. 14, 2024, Augmented Reality Assistance for Osteotomy and Discectomy.
U.S. Appl. No. 18/684,756, filed Feb. 19, 2024, Registration and Registration Validation in Image-Guided Surgery.
U.S. Appl. No. 18/693,338, filed Mar. 19, 2024, Surgical Planning and Display.

(56) References Cited

OTHER PUBLICATIONS

U.S. Appl. No. 18/365,566, filed Aug. 4, 2023, Systems for Medical Image Visualization.
U.S. Appl. No. 18/399,253, filed Dec. 28, 2023, Methods for Medical Image Visualization.
U.S. Appl. No. 18/398,837, filed Dec. 28, 2023, Adjustable Augmented Reality Eyewear for Image-Guided Medical Intervention.
U.S. Appl. No. 18/399,433, filed Dec. 28, 2023, Configurable Augmented Reality Eyewear for Image-Guided Medical Intervention.
U.S. Appl. No. 35/508,942 U.S. Pat. No. D 930,162, filed Feb. 13, 2020 Sep. 7, 2021, Medical Headset.
Lumus Ltd., "DK-32 See-through Wearable Display Development Kit", Rehovot, Israel, pp. 1-2, Dec. 24, 2013.
Liao et al., '3-D Augmented Reality for MRI-Guided Surgery Using Integral Videography Autostereoscopic Image Overlay', IEEE Transactions on Biomedical Engineering, vol. 57, No. 6, pp. 1476-1486, Feb. 17, 2010.
Hainich et al., "Near-Eye displays", Chapter 10 of Displays: Fundamentals and Applications, CRC press, pp. 439-504, Jul. 5, 2011.
Brainlab—Image Registration Options Enhanced Visualization Leveraging More Data , pp. 1-4, Feb. 2019.
Liu et al., "Marker orientation in fiducial registration", Medical Imaging 2003: Image Processing, Proceedings of SPIE vol. 5032, pp. 1176-1185, 2003.
Fingas, "Fraunhofer iPad app guides liver surgery through augmented reality", pp. 1-6, Aug. 22, 2013.
Sagitov et al., "Comparing Fiducial Marker Systems in the Presence of Occlusion", International Conference on Mechanical, System and Control Engineering (ICMSC), pp. 1-6, 2017.
U.S. Appl. No. 16/419,023 Office Action dated Jul. 22, 2021.
Wolf et al., U.S. Appl. No. 17/015,199, filed Sep. 9, 2020.
Gera et al., U.S. Appl. No. 16/901,026, filed Jun. 15, 2020.
U.S. Appl. No. 16/200,144 Office Action dated Sep. 18, 2021.
International Application # PCT/IB2021/055242 Search Report dated Oct. 7, 2021.
International Application PCT/IB2022/059030 filed Sep. 23, 2022.
International Application PCT/IB2022/056986 search report dated Dec. 7, 2022.
JP Application # 2021525186 Office Action dated Dec. 1, 2021.
EP Application # 19796580.9 Search Report dated Dec. 20, 2021.
International Application # PCT/IB2021/058088 Search Report Dec. 20, 2021.
Mitrasinovic et al., "Clinical and surgical applications of smart glasses", pp. 381-401, Technology and Health Care, issue 23, year 2015.
Martin-Gonzalez et al., "Head-mounted virtual loupe with sight-based activation for surgical applications", IEEE symposium on mixed and augmented reality, pp. 207-208, Oct. 19-22, 2009.
Figl et al., "A fully automated calibration method for an optical see-through head-mounted operating microscope with variable zoom and focus", pp. 1492-1499, IEEE transactions on medical imaging, vol. 24, No. 11, Nov. 2005.
Medithinq Co. Ltd., "Metascope: world's first wearable scope", pp. 1-7, Jan. 2023.
Martin-Gonzalez et al., "Sight-based magnification system for surgical applications", pp. 26-30, Conference proceedings of Bildverarbeitung für die Medizin, year 2010.
Burstrom et al., "Frameless patient tracking with adhesive optical skin markers for augmented reality surgical navigation in spine surgery", SPINE, vol. 45, No. 22, pp. 1598-1604, year 2020.
Suenaga et al., "Vision-based markerless registration using stereo vision and an augmented reality surgical navigation system: a pilot study", BMC Medical Imaging, pp. 1-11, year 2015.
Mayfield Clinic, "Spinal Fusion: Lateral Lumbar Interbody Fusion (LLIF)", pp. 1-6, Jan. 2021.
Qian et al., "AR-Loupe: Magnified Augmented Reality by Combining an Optical See-Through Head-Mounted Display and a Loupe", pp. 2550-2562, IEEE Transactions on Visualization and Computer Graphics, vol. 28, No. 7, Jul. 2022.
Kazanzides et al., "Systems and Methods for Augmented Reality Magnifying Loupe", case ID 15944, pp. 1-2, Nov. 26, 2020.
U.S. Appl. No. 16/724,297 Office Action dated Nov. 4, 2021.

\* cited by examiner

ROTATING MARKER AND ADAPTER FOR IMAGE-GUIDED SURGERY

FIELD OF THE INVENTION

The present invention relates generally so a marker and a marker adapter for image-guided surgery, and particularly to a marker that may be attached to a patient and to a marker adapter that allow multiple orientations of the marker.

BACKGROUND OF THE INVENTION

During image guided surgery, it is important to register elements of a patient, upon whom the surgery is being performed, with equipment generating the image. This is typically the case where the surgery comprises an augmented reality system, which generates images of portions of the patient that are in registration with the actual portions.

In order to register the elements of the patient, and keep the registration, a patient marker may be fixedly attached to the patient. An initial image of a marker may be analyzed, and used to provide the registration. So long as a marker continues to be fixedly attached to the patient at the same location, the registration remains valid and may be used to track the patient. However, if the marker is moved and then re-attached, for example to provide access to the patient, the registration typically needs so be repeated.

Documents incorporated by reference in the present patent application are so be considered an integral part of the application except chat, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a patient marker for image guided surgery that is configured to be coupled to an anchoring device via a base, the base having a base axis, base connections and a first indicator, the patient marker including:
  an adapter having a first surface having first surface adapter connections configured to mate with the base connections, and a second surface, opposite the first surface, having second surface adapter connections congruent with the base connections, and at least one second indicator; and
  an alignment target, including:
  a target region having an alignment pattern formed thereon; and
  a socket connected to the target region and having socket connections congruent with the first surface adapter connections, so that:
  in a first configuration of the marker, the socket is coupled to the base by mating the first surface adapter connections with the base connections and mating the socket connections with the second surface adapter connections, and
  in a second configuration of the marker, the socket is fit onto the base by mating the socket connections with the base connections,
  whereby an angle of orientation of the alignment target about the base axis is indicated by one of the first indicator and the at least one second indicator.

Typically, in any given configuration of the marker, only one of the first indicator and the at least one second indicator is accessible.

In a disclosed embodiment in the first configuration the alignment target fits to the adapter in a plurality of discrete orientations. The discrete orientations may consist of two orientations at 180° to each other.

In a further disclosed embodiment in the second configuration the alignment target fits to the base in a plurality of discrete orientations. The discrete orientations may consist of two orientations at 180° to each other.

In a yet further disclosed embodiment in the first configuration the angle of orientation includes a first pair of angles at 180° to each other, and in the second configuration the angle of orientation includes a second pair of angles at 180° to each other and at 90° to the first pair of angles.

In an alternative embodiment the base connections and the first surface adapter connections are configured so that the adapter mates with the base in one single orientation.

In a further alternative embodiment the at least one second indicator is a divot that acts as a verification point.

In a yet further alternative embodiment the at least one second indicator is formed as an extension of a surface of the adapter.

In a still further alternative embodiment one of the at least one second indicator is positioned so that it aligns with and prevents access to the first indicator, while the first surface adapter connections are mated with the base connections.

The at least one second indicator may consist of two indicators. The angle between lines from each of the two indicators to a central hole of the adapter may be obtuse.

The at least one second indicator may be configured to be touched by a tip of a tool used in the surgery.

There is further provided, according to an embodiment of the present invention, a method for producing a patient marker to be coupled to an anchoring device via a base, the base having a base axis, base connections and a first indicator, the method including:
  configuring first surface adapter connections of an adapter having a first surface to mate with the base connections;
  forming on a second surface of the adapter, opposite the first surface, second surface adapter connections congruent with the base connections, and at least one second indicator; and
  providing an alignment target, consisting of:
  a target region having an alignment pattern formed thereon, and
  a socket connected to the target region and having socket connections congruent with the first surface connections, so that:
  in a first configuration of the marker, the socket is coupled to the base by mating the first surface adapter connections with the base connections and mating the socket connections with the second surface adapter connections, and
  in a second configuration of the marker, the socket is fit onto the base by mating the socket connections with the base connections,
  whereby an angle of orientation of the alignment target about the base axis is indicated by one of the first indicator and the at least one second indicator.

There is further provided, according to an embodiment of the present invention, an adapter for providing additional orientations to a patient marker with respect to an anchoring device in image guided surgery, wherein the an device has a base having a base axis and a first indicator, the adapter including:

a first surface configured to be coupled to the base;
a second surface, opposite the first surface, configured to be coupled to the patient marker; and
at least one second indicator,
wherein the patient marker is coupled to the base by coupling the first surface of the adapter with the base and coupling the patient marker with the second surface of the adapter, and wherein when the patient marker is coupled to the anchoring device via the adapter:
an angle of orientation of the patient marker about the base axis is indicated by only one of the at least one second indicator, and
the first indicator is not accessible.

Typically, the at least one second indicator consists of two indicators, and wherein when the patient marker is coupled to the anchoring device via the adapter, only one of the two indicators is accessible. Additionally or alternatively, the at least one second indicator may be configured to be touched by a tip of a tool used in the surgery and serve as a verification point.

The present invention will be more fully understood from the following detailed description of the embodiments thereof, taken together with the drawings in which:

BRIEF DESCRIPTION OF THE DRAWING

FIGS. 3A, 3B, 35, and 3D illustrate four orientations of a target of the patient marker with respect to a clamp, according to an embodiment of the present invention;

DETAILED DESCRIPTION OF EMBODIMENTS

Overview

Figure 1:
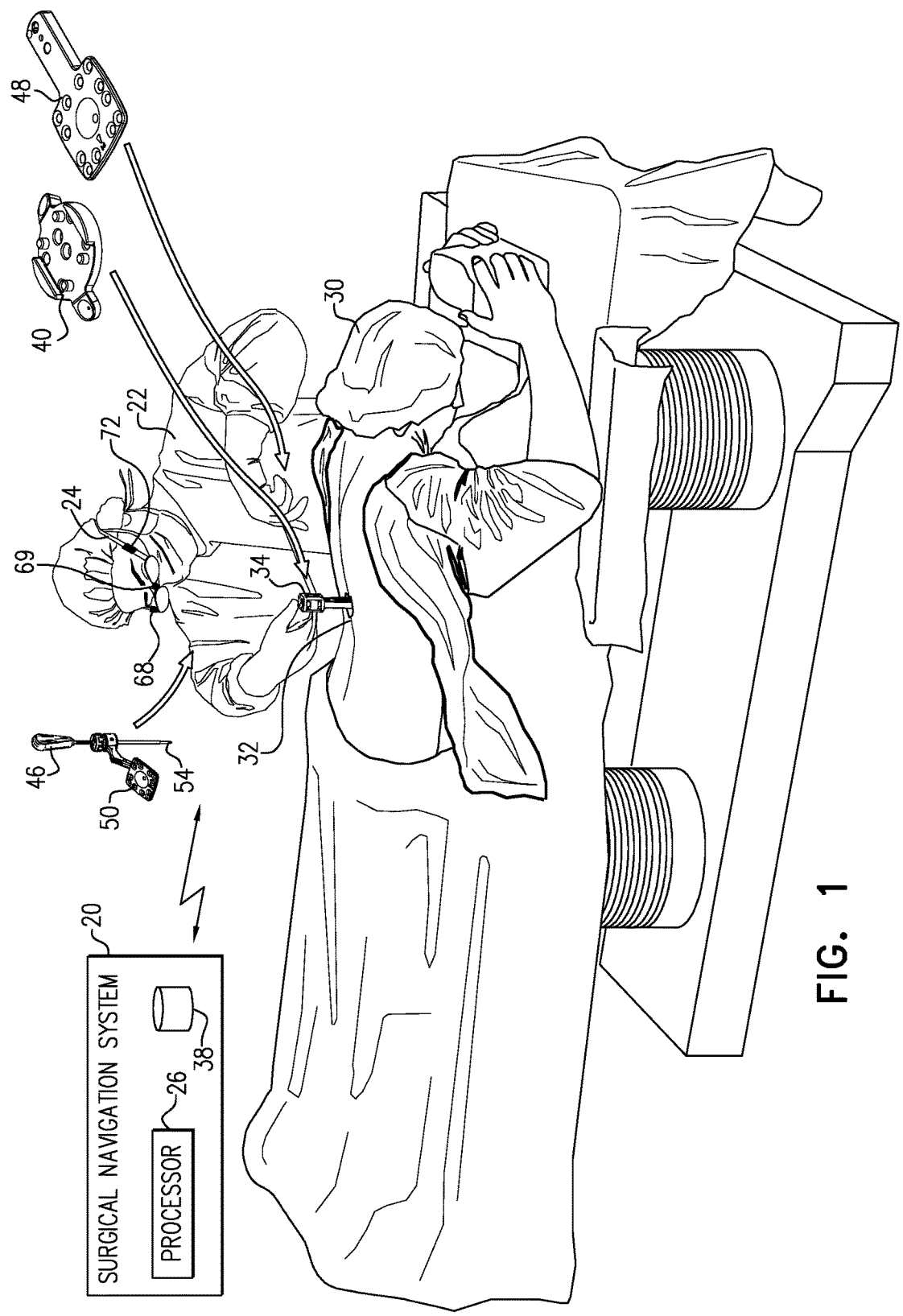
FIG. 1 is a schematic illustration of a medical procedure, according to an embodiment of the present invention.

In an augmented reality system that is used for a medical procedure performed on a patient, the position of the patient in relation to an augmented reality assembly worn by a professional performing the procedure needs to be tracked, so that images presented in the assembly align with the patient. To implement the tracking, a patient marker, comprising optical elements, may be fixedly attached to the patient, and a camera in the assembly may be configured to image the elements. A processor may then analyze the image so as to track the marker. As long as the marker is fixed to the patient, the processor may use the tracking of the marker to track the patient.

However, during the procedure the patient marker may interfere with the professional's access to the patient, and/or the professional's view of the patient, necessitating adjustment of the patient marker.

Embodiments of the present invention provide a patient marker which may be adjusted, while not requiring any new image analysis of the optical elements of the marker to continue the tracking.

A disclosed embodiment of the present invention provides a patient marker comprising a base connecting to an anchoring device, herein by way of example assumed to comprise a clamp. The clamp has jaws configured to grip a bone of the patient, such as a spinous process. Once the jaws have gripped the bone of the patient, the base provides a rigid platform to which may be attached an alignment target that does not move relative to the patient's bone.

The alignment target may be attached, in a first configuration of the marker, directly to the base in one of a first plurality of preselected orientations. An image of the alignment target may then be acquired by the camera in the augmented reality assembly worn by the professional, to implement tracking of the target and of the patient. The target may be adjusted between the first plurality of preselected orientations, without requiring any new image analysis by the processor of the imaged target, so that the processor may continue the tracking.

To provide further orientations of the target, embodiments of the invention provide an adapter. Rather than attaching the target directly to the base, as in the first configuration described above, in a second configuration of the marker the target is attached to the adapter which is then attached to the base.

The adapter provides the target with a second plurality of preselected orientations, different from the first plurality. As for the first configuration, the target may be adjusted between the second plurality of preselected orientations, without requiring any new image analysis, so that the processor may continue the tracking.

In addition, the adapter is configured so that the first and second plurality of preselected orientations are simply related. In a disclosed embodiment the first plurality of configurations, which does not use the adapter, provides a first orientation wherein the target rotates 0° about a base axis and a second orientation wherein the target rotates 180° about the axis. The second plurality of configurations, which uses the adapter, provides a third orientation where the target rotates 90° about the axis and a fourth orientation where the target rotates 270° about the axis.

Since the alignment target may be attached, with or without use of the adapter, to the base in a multiplicity of preselected orientations, embodiments of the invention provide a simple and cost effective solution for adjusting the patient marker without requiring new image analysis of the target.

According to some aspects, an adapter, as described above, is provided, which allows further orientations to a marker. The adapter provides additional orientations to the patient marker with respect to the anchoring device. The base (referred to above) connecting to the anchoring device, or comprised in the anchoring device, is provided by the anchoring device, and the base has a base axis and a first indicator.

The adapter has two surfaces: a first surface that may be coupled to the base, e.g., by the first surface adapter connections, and a second surface, opposite the first surface, that may be coupled to the patient marker, e.g., via the second surface adapter connections. The adapter also has at least one, e.g., two, second indicators. The patient marker may be coupled to the base by coupling the first adapter surface to the base, and coupling the second adapter surface to the patient marker, so that the patient marker couples to the anchoring device via the adapter.

Figure 3A:
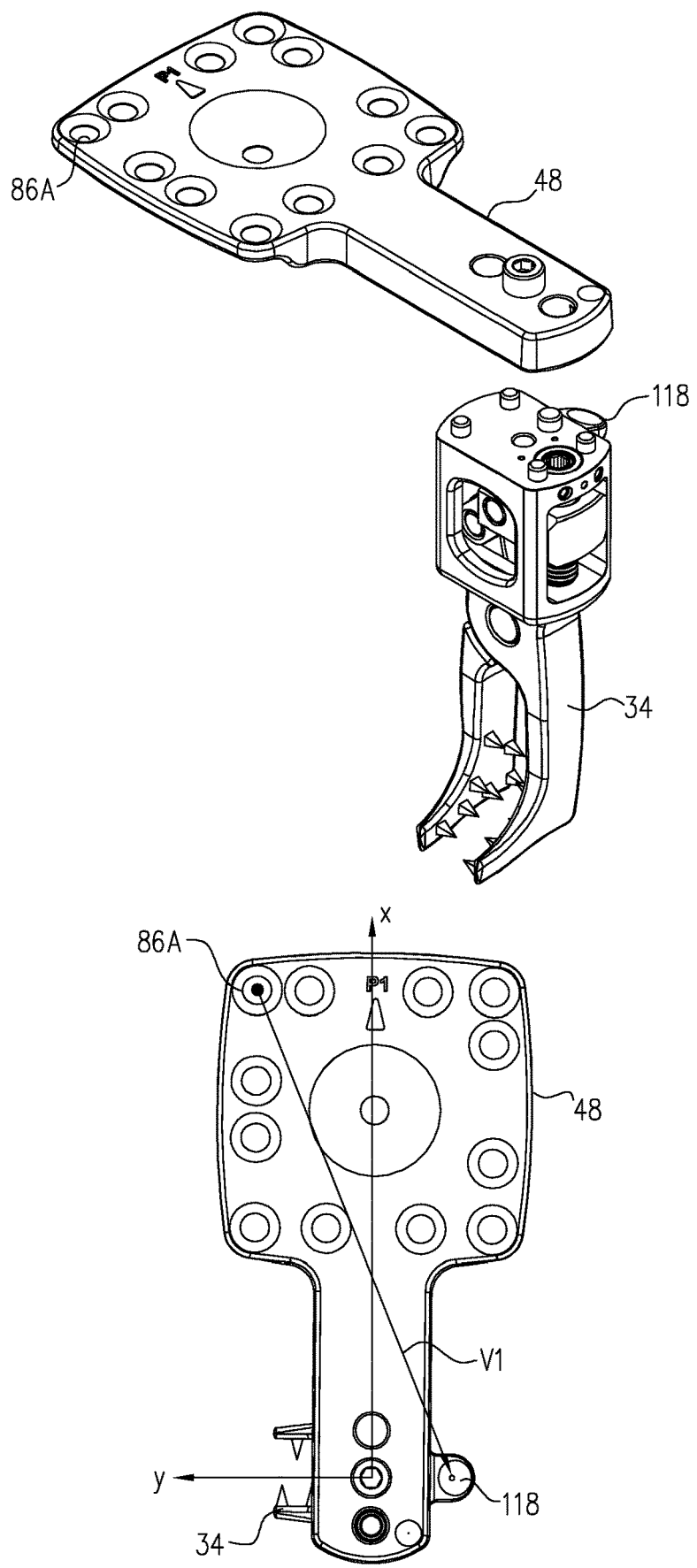
Figure 3B:
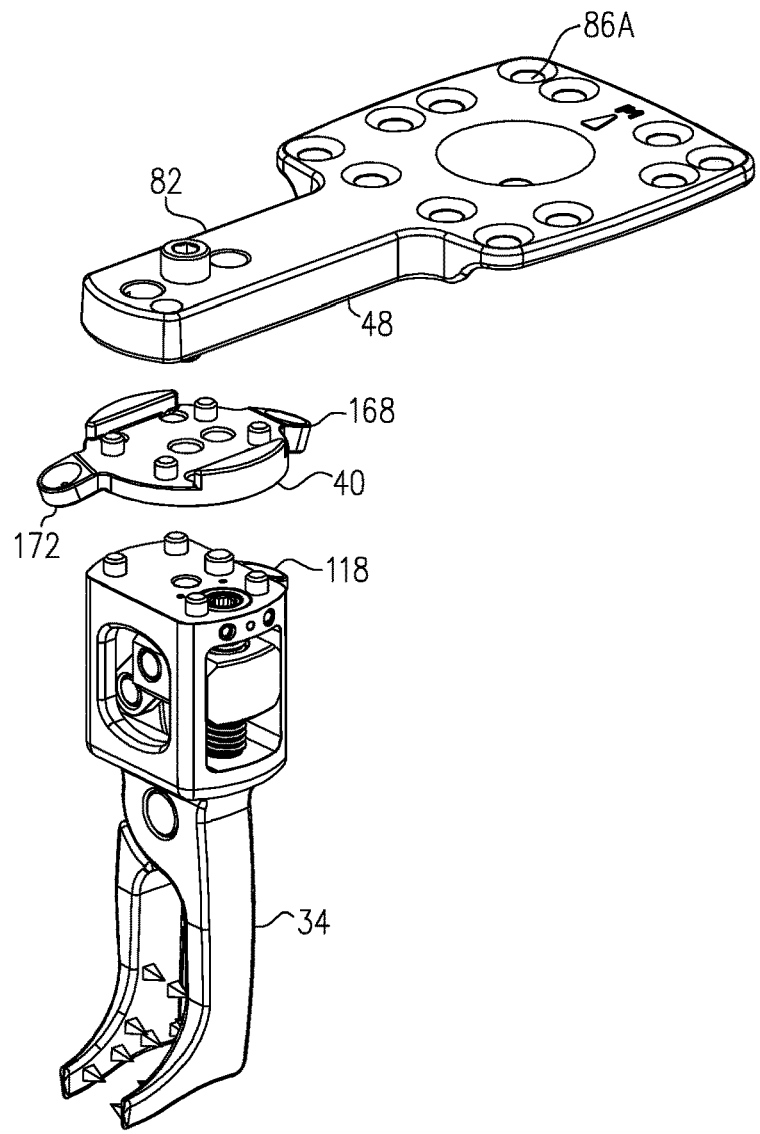
Figure 3B:
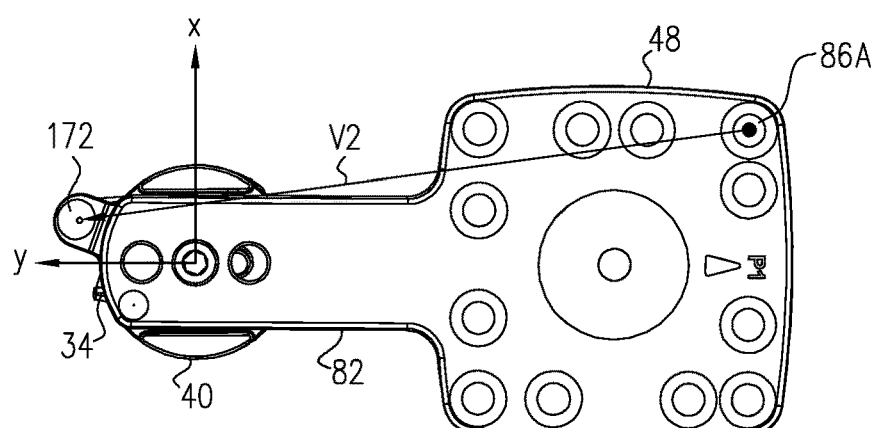
Figure 3C:
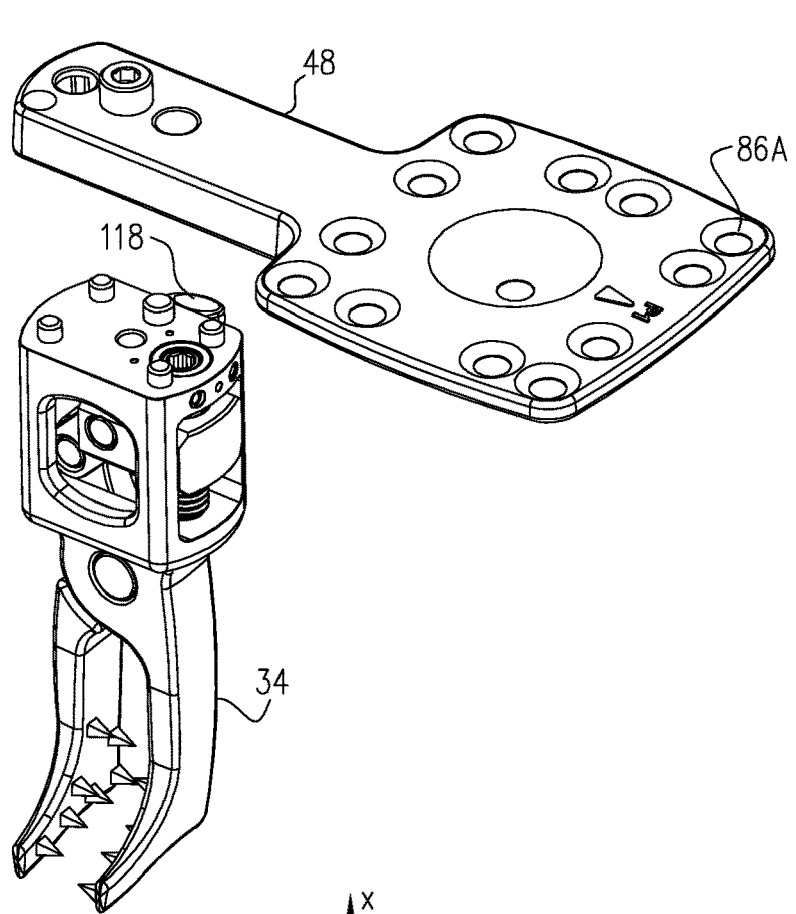
Figure 3C:
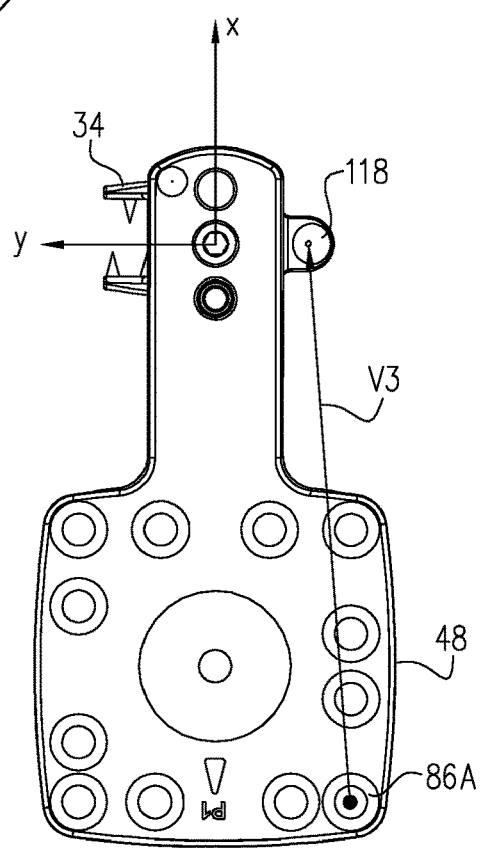
Figure 3D:
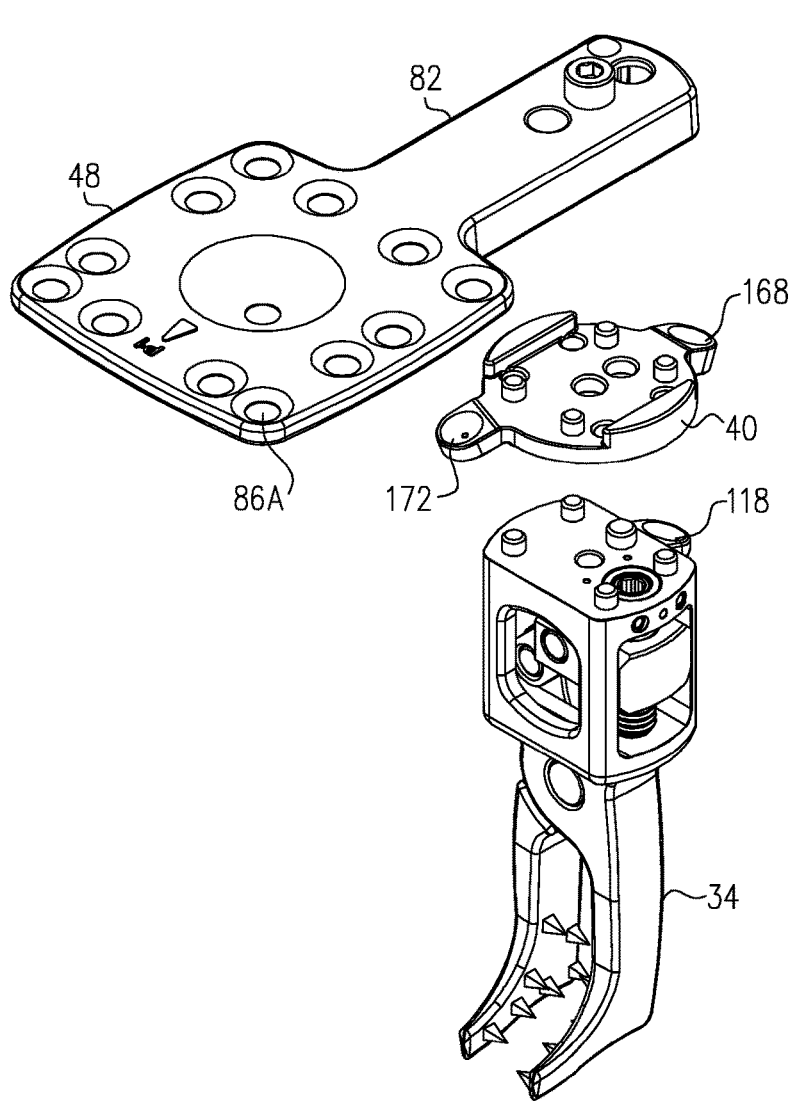
Figure 3D:
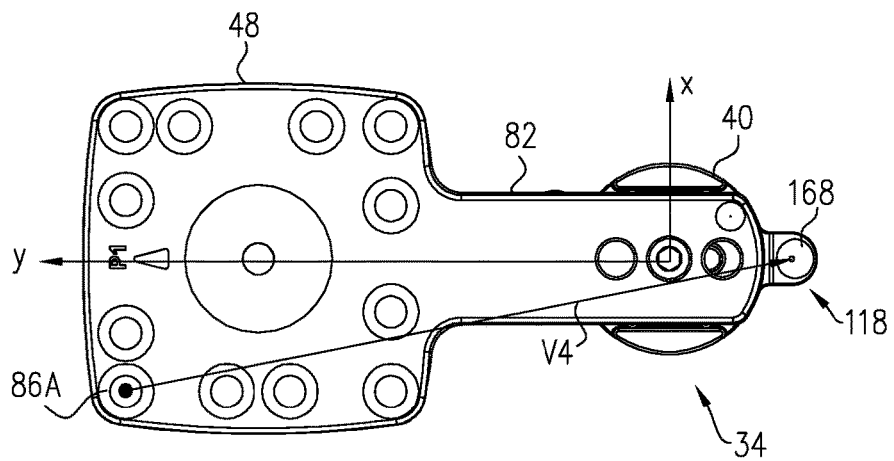

When the patient marker is coupled to the anchoring device as described above, the angle of orientation of the patient marker about the base axis is indicated by only one of the second indicators. For example, in case of two adapter indicators, when the marker is coupled to the adapter, only one indicator is accessible while the other is covered by the marker (e.g., positioned beneath the marker as exemplified in FIGS. 3B and 3D). Furthermore, the first indicator is not accessible (e.g., covered by the adapter, as shown in FIGS. 3B and 3D).

The adapter may be coupled to the anchoring device via its base and may be coupled to the marker; it may be formed, configured to and operate, all as detailed herein above and herein below, with the necessary changes.

During the medical procedure, in addition to tracking the patient marker, a position of the tip of a tool used in the procedure is also tracked. The base of the anchoring device has a verification point or divot fixedly located, in a known preselected position in the base. The adapter also has at least one, and herein by way of example two verification points, fixedly located in known preselected positions on the adapter.

To identify, during the procedure, which of the preselected orientations of the target is operative, the tool tip is placed on, or in proximity to, one of the verification points of the base or the adapter. The processor of the augmented reality system calculates a vector between the indicated verification point and the tracked alignment target, and from the vector (which is different for all the target orientations) identifies the orientation of the target.

DETAILED DESCRIPTION

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Reference is now made to FIG. 1, which is a schematic illustration of a medical procedure, according to an embodiment of the present invention. During the procedure, performed by a professional 22, the professional uses a surgical navigation system 20, which assists the professional in performance of the procedure. Surgical navigation system. 20 comprises a processor 26, which operates elements of the system, and which communicates with an augmented reality assembly 24, comprising a set of augmented reality spectacles worn by professional 22, and that is incorporated in the system. Assembly 24 comprises, inter alia, an image capturing device 72, also termed herein a camera 72, that has a field of view 76 and that is configured to capture images in the visible spectrum. Assembly 24 also comprises an image capturing device 68, also termed a camera 68, that is operative in the non-visible spectrum, typically the infra-red, as well as a projector 69 that projects radiation in the operative spectrum of device 68. Functions of system. 20, processor 26, and device 72 are described below. An assembly similar to augmented reality assembly 24, and its operation, are described in U.S. Pat. No. 9,928,629, to Benishti, et al., whose disclosure is incorporated herein by reference.

It will be understood that the present invention includes augmented reality assemblies other than assembly described here. One example of such an alternative assembly is described with reference to FIG. 5, and all such assemblies are assumed to be comprised within the scope of the present invention.

In one embodiment processor 26 is assumed to be incorporated within a stand-alone computer, and the processor typically communicates with other elements of the system, including assembly 24, wirelessly, as is illustrated in FIG. 1. Alternatively or additionally, processor 26 may use optical and/or conducting cables for the communication. In further alternative embodiments processor 26 is integrated within assembly 24, or in the mounting of the assembly. Processor 26 is typically able to access a database 38, wherein are stored images and other visual elements used by system 20. Software enabling processor 26 to operate system 20 may be downloaded to the processor in electronic form, over a network, for example. Alternatively or additionally, the software may be provided on non-transitory tangible media, such as optical, magnetic, or electronic storage media.

The medical procedure exemplified here is performed on a patient 30, and during an initial stage of the procedure professional 22 makes an incision 32 into the Patient's back. The professional then inserts an anchoring device 34, herein assumed to comprise a spinous process clamp 34, into the incision, so that opposing jaws of the clamp are located on opposite sides of the spinous processes. The professional adjusts the clamp to grip one or more spinous processes, selected by the professional, of the patient. The professional may then attach an orientation adapter 40 to a base 44 (illustrated in FIG. 2A) of the clamp, and an alignment target 48 to the adapter, the target when attached to the base via the adapter operating as a patient marker 52 (illustrated in FIG. 2A). Patient marker 52 thus comprises alignment target 48 coupled, as described herein, to base 44. As is described below, processor 26 tracks alignment target 48 of patient marker 52, and the tracking is used by system 20 to determine the position and orientation of patient 30 during the medical procedure.

During the procedure professional 22 uses a tool 46 comprising a tool marker 50. Processor 26 also tracks tool 46 using tool marker 50 attached to the tool, and because the dimensions of the tool and the tool marker are known, the tracking provides the processor with the position of a tool tip 54 of the tool. A tool and tool marker similar to tool 46 and marker 50 are described in U.S. application Ser. No. 17/015,199, which is incorporated herein by reference.

During the procedure, it may be necessary for professional 22 to adjust the position of target 48, typically to enable the professional to more easily access elements of patient 30. Embodiments of the present invention facilitate such adjustment, by providing a plurality of different discrete orientations of alignment target 48 with respect to clamp 34. Each of the orientations may be identified by processor 26 from an acquired image of target 48 and from the tracked position of tool tip 54, as is described below. In addition, as is described below, once patient marker 52 has been through art initial setup process to align images presented in assembly 24 with patient 30, processor 26 may maintain the image alignment for the different identified orientation changes, by virtue of the fact that dimensions of target 48, adapter 40, and base 44 are known.

Figure 2A:
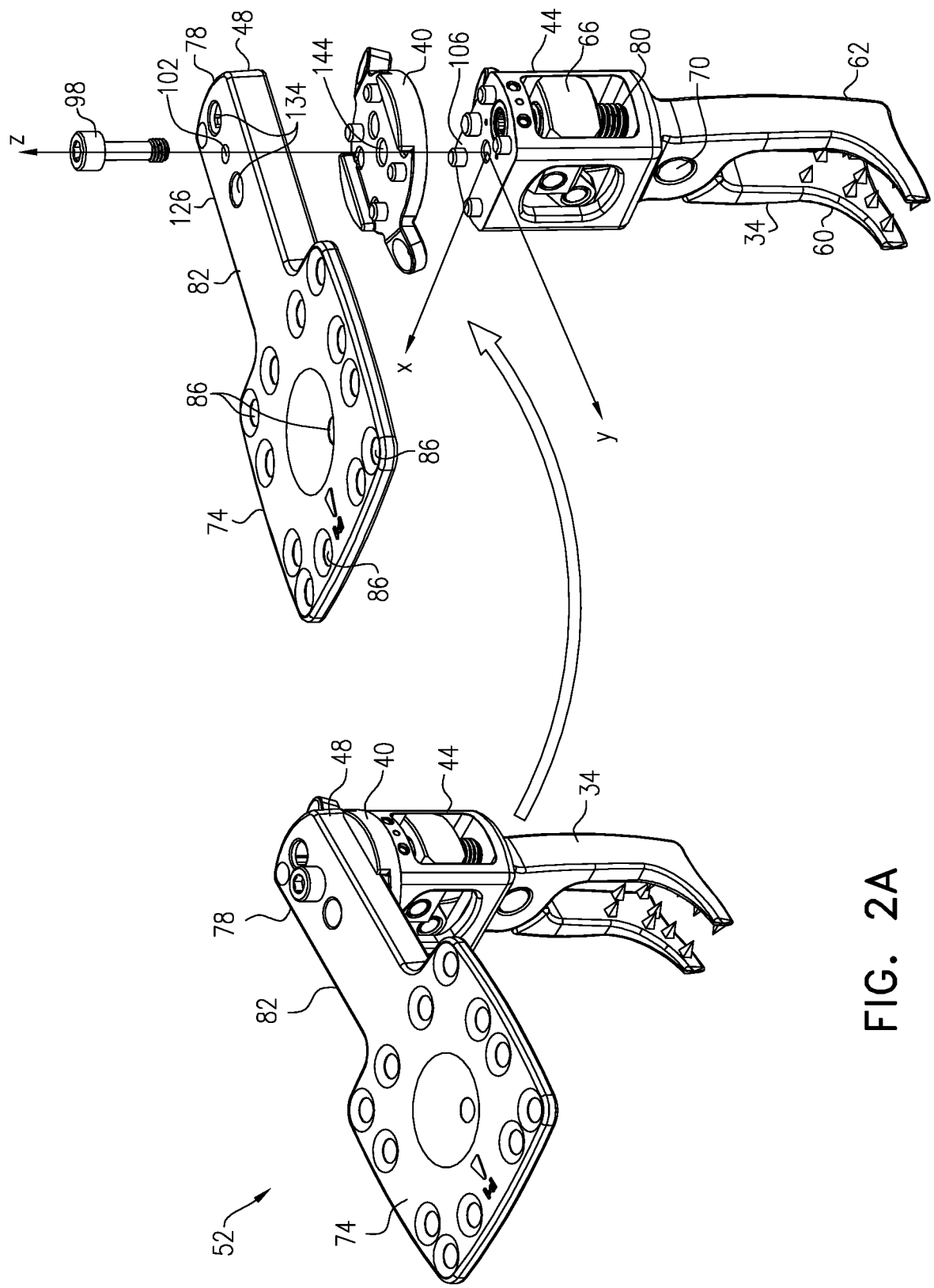
FIG. 2A illustrates elements of a patient marker, in an assembled and a partly exploded format.
Figure 2B:
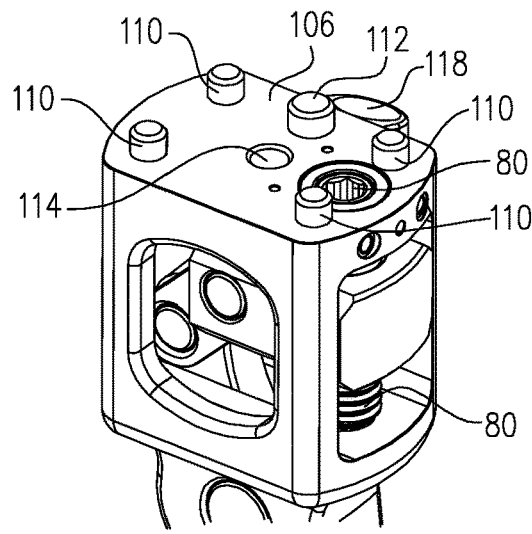
FIGS. 2B, 2C, and 2D illustrate elements of portions of the marker, according to an embodiment of the present invention.
Figure 2C:
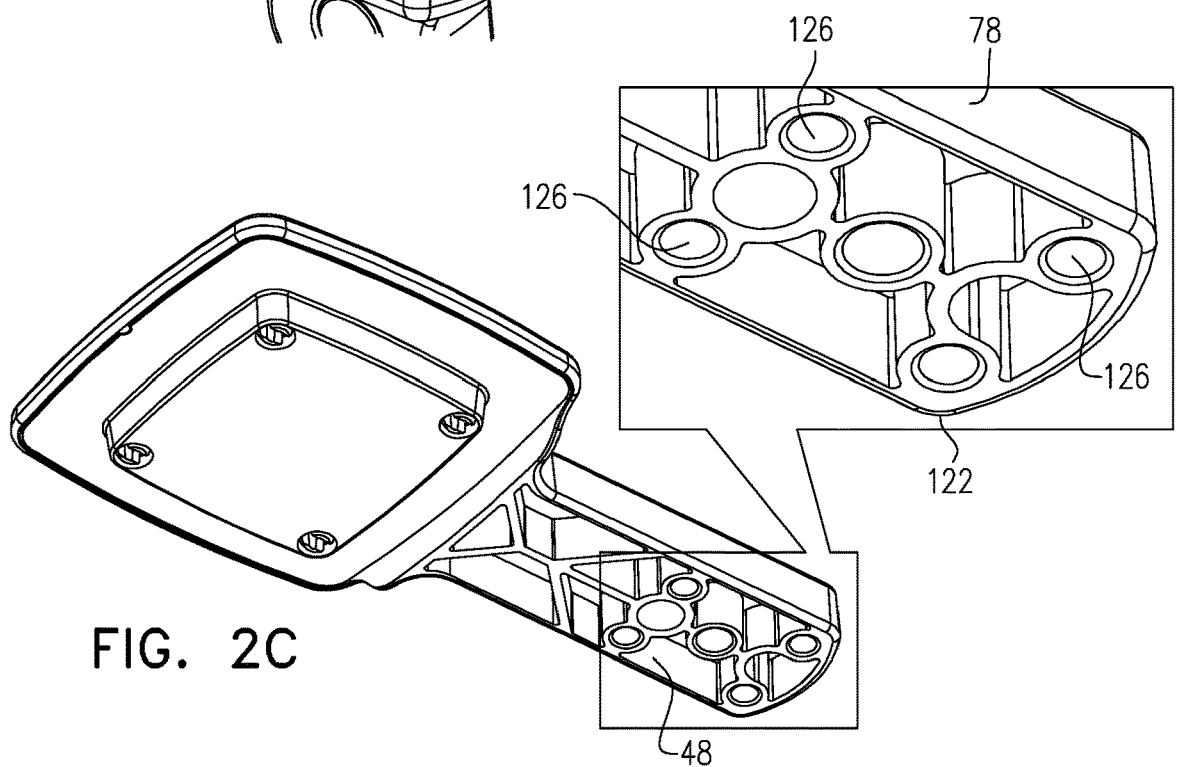
Figure 2D:
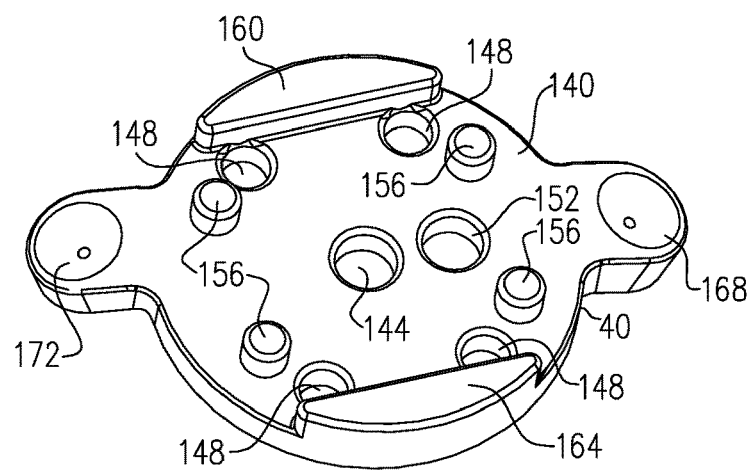

FIG. 2A illustrates elements of patient marker 52, in an assembled and a partly exploded format, and FIGS. 23, 2C, and 2D illustrate elements of portions of the marker, according to an embodiment of the present invention. As stated above, marker 52 is formed by attaching alignment target. 48 to adapter 40, which is in turn attached to base 44 of clamp 34. The clamp is described below.

Clamp 34 comprises a pair of laws 60, 62 in a lower section of the clamp. The jaws are coupled to clamp base 41 in an upper section of the clamp, the base comprising a jaw adjustment mechanism 66. In the embodiment described herein, jaw 62 is fixed to base 44, and jaw 60 moves with respect to jaw 62, by being rotated about a hinge pin 70. Jaw adjustment mechanism 66 comprises an adjustment screw 80, which is coupled by a lever to jaw 60 so that rotation of the screw causes jaw 60 to approach or retreat from jaw 62. Thus professional 22 is able to cause the jaws of clamp 34 to grip or release a bone, such as one or more spinous processes, by rotating screw 80.

Alignment target 48 comprises a target region 74 and a socket 78, the target region and the socket being fixedly connected together by a connecting beam 82. Alignment target 48, together with its components target region 74 and socket 78, are generally planar. Target region 74, by way of example, is approximately rectangular and comprises optical elements 36. Elements 86 are arranged in a three-dimensional (3D) pattern, although in some embodiments the elements may be in a two-dimensional (2D) pattern, with no rotational axis of symmetry (other than a trivial axis of symmetry for rotating by 360°), and no mirror plane of symmetry, so that an image of the elements enables an unambiguous determination of the location and orientation of the target region. Elements 86 are typically retroreflectors. An entity with an arrangement of optical elements similar to the arrangement herein is described in U.S. patent application Ser. No. 16/901,026, which is incorporated herein by reference.

For clarity, in the description herein, elements of marker 52 are assumed, by way of example, to be referenced to a Cartesian set of orthogonal xyz axes, with origin at the center of an upper plane surface 106 of base 44, as illustrated in FIG. 2A. A z-axis is assumed to be orthogonal to plane surface 106, a y-axis is assumed to be parallel to a symmetry axis of hinge 70, and an x-axis is assumed to be orthogonal to the y and z axes.

As stated above, socket. 78 is generally planar, and has a central hole 102. As is explained below, socket 78 and adapter 40 are fixed to base 44 by a captive screw 98 that penetrates a socket central hole 102 and also an adapter central hole 144. Holes 102 and 144 are dimensioned as clearance holes for screw 98.

FIG. 2B illustrates upper surface 106 of base 44. Surface 106 comprises a threaded hole 114 at the center of the surface, that accepts screw 98. Surface 106 also comprises four substantially similar cylindrical protuberances 110 located at the corners of a non-square rectangle, and distributed symmetrically about hole 114. As described below, protuberances 110 act as connections for base 44. There is a cylindrical protuberance 112 that in the illustrated embodiment is centered on a longer side of the non-square rectangle, and chat is larger than protuberances 110. Extending from base 44, and fixed to the base, is a divot. 118 that acts as a verification point or indicator and that is herein also termed divot indicator 118 or just indicator 118. There is an aperture in surface 106 that provides access to screw 80.

FIG. 25 illustrates a lower surface 122 of socket 73, and an upper surface of the socket is shown in FIG. 2A. Lower surface 122 comprises four cylindrical recesses 126 that are dimensioned and positioned to accept protuberances 110 of surface 106, when socket 78 is placed on surface 106, so that recesses 126 also act as connections. An upper surface 126 of the socket comprises two access holes 134, distributed symmetrically about clearance hole 102. In addition, when socket 78 is mated with surface 106, clearance hole 102 aligns with threaded hole 114, so that crew 98 may be used to attach the socket, and thus the target, to base 44.

The description above, of target 48 being directly attached to surface 106, i.e., without adapter 40 being used, corresponds to a first configuration of marker 52. It will be understood that because of the rectangular symmetry of recesses 126 and protuberances 110, there are two possible orientations of target 48 with respect to clamp 34, when the target is attached to base 44 in this first configuration. A partially exploded view of each orientation is shown in FIG. 3A and FIG. 3C.

FIG. 2D illustrates an upper surface 140 of adapter 40. Adapter 40 is generally circular, and clearance hole 144 is located at the center of the adapter. Adapter 40 comprises four cylindrical holes 148 that are dimensioned and positioned to accept protuberances 110 of surface 106, when the adapter is placed on surface 106. Holes 148 are distributed symmetrically about central clearance hole 144, and it will be understood that holes 148 form a non-square rectangle. Holes 148 penetrate to a lower surface of adapter 40, and act as connections. To enable the placement referred to above, adapter also comprises a fifth cylindrical hole 152, that is dimensioned and positioned to accept protuberance 112 when holes 148 connect with, i.e., mate with, protuberances 110.

Four cylindrical protuberances 156 are formed on surface 110, and they are arranged to be congruent to protuberances 110, and thus lie in a non-square rectangle. Protuberances 156 are distributed symmetrically about central hole 114, and are located so that the non-square rectangle they form is orthogonal to the non-square rectangle formed by holes 148. As for protuberances 110, protuberances 156 act as connections.

In operation of marker 52 (illustrated in FIGS. 2A-2D) using adapter 40, the adapter is first placed on surface 106 of base 44 so that holes 148 mate with protuberances 110, and so that hole 152 mates with protuberance 112. It will be understood that for this mating there is only one possible orientation of the adapter with respect to base 44, and that in this orientation clearance hole 144 aligns with threaded hole 114 of the base.

Once adapter 40 has been placed on surface 106, socket 78 of target 48 may be mated with the upper surface of the adapter, by pushing recesses 126 of the socket onto protuberances 156. The mating is facilitated by forming retaining shoulders 160, 164 on the surface of the adapter, symmetrically on either side of hole 144, the shoulders having internal walls that are separated by the width of socket 78, together with a clearance value.

The description above, of target 48 being attached to surface 106 via adapter 40, corresponds to a second configuration of marker 52. It will be understood that in this second configuration, there are two possible orientations of target 48 with respect to clamp 34, when the target is attached to adapter 40. A partially exploded view of each orientation of the second configuration is shown in FIG. 3B and FIG. 3D.

First and second divots 168, 172, which act as verification points or indicators and which are also herein termed first and second divot indicators 168, 172, or just indicators 168, 172, are formed in adapter 40 as extensions of surface 140. First indicator 168 is positioned so that it aligns with, and prevents access to, indicator 118 when the adapter is attached to surface 106. Second indicator 172 is positioned so that the angle between a line segment from indicator 172 to central hole 144 and a line segment from indicator 168 to the central hole is an obtuse angle, less than 180°. In a disclosed embodiment the angle is approximately 160°, but other angles are possible. Positioning of second indicator 172 is referred to further below.

As stated above, marker 52 has two possible configurations, and for each configuration target 48 has two possible orientations with respect to clamp 34. There are thus four different orientations of target 48 with respect to the clamp. As is described below, using images of optical elements 86 of target. 48, and being provided with the positions of indicators 113, 163, or 172, processor 26 is able to identify in which of the four orientations target 48 is. As is also described below, the processor is able to adjust the images presented to the professional in the augmented reality assembly to compensate for any change in the orientation.

FIGS. 3A, 3B, 3C, and 3D illustrate the four possible orientations of target 48 with respect to clamp 34, according to an embodiment of the present invention. In each of the figures, marker 52 is drawn as a partially exploded view of the marker, and also as a top-down, i.e., down the z-axis, view of the marker. From consideration of the figures, and of the construction of the elements of marker 52 described above, it will be understood that in each of the four orientations target 48 is rotated clockwise by a multiple of 90° from the x-axis, i.e., in FIG. 3A by 0°, in FIG. 3B by 90°, in FIG. 3C by 180°, and in FIG. 3D by 270°. The orientations are also referred to herein as the 0°, 90°, 180°, and 270° orientation.

In the first configuration of the marker, i.e., when adapter 40 is not used, corresponding to FIGS. 3A and 3C and the 0° and 180° orientations, the only indicator present, and thus accessible, is indicator 118 of base 44.

In the second configuration of the marker, when adapter 40 is used, corresponding to FIGS. 3B and 3D and the 90° and 270° orientations, all three indicators 118, 168, and 172, are present. However, the indicators of adapter 40 are arranged so that only one of indicators 118, 168, and 172 is accessible. Thus, in the 90° orientation illustrated in FIG. 3B, indicators 118 and 168 are obscured by connecting beam 82, and only indicator 172 is accessible. In the 270° orientation illustrated in FIG. 3D, indicator 172 is obscured by connecting beam 82, and indicator 168 obscures indicator 118 of base 44, so that only indicator 168 is accessible.

It will be appreciated that in each of the four possible orientations, only one indicator is accessible.

Using the locations of the accessible indicators, for each orientation processor 26 calculates respective vector from a preselected point on target 48 to the accessible indicator. In the figures, the preselected point is assumed to be an optical element 86 at a corner of target 48, herein termed element 86A, but any other convenient preselected point on the target, such as a center of the target, may be used. As shown in the figures, for orientations 0°, 90°, 180°, and 270° there are respective vectors V1, V2, V3, and V4.

Table I below illustrates the orientations, vectors and parameters associated with the vectors. The vector parameters are assumed to comprise ordered triples, as measured with respect to the xyz axes described above.

TABLE I

| Orientation | Vector | Vector Parameters |
|---|---|---|
| 0° | V1 | $(x_1, y_1, z_1)$ |
| 90° | V2 | $(x_2, y_2, z_2)$ |
| 180° | V3 | $(x_3, y_3, z_3)$ |
| 270° | V4 | $(x_4, y_4, z_4)$ |

Table II below gives a numerical example, according to a disclosed embodiment, of approximate vector parameters, in mm., for the different orientations.

TABLE II

| Orientation | Vector | Vector Parameters |
|---|---|---|
| 0° | V1 | (−103, −42, −13) |
| 90° | V2 | (−17, +124, −8) |
| 180° | V3 | (+103, +8, −13) |
| 270° | V4 | (+25, −126, −8) |

Since the dimensions of all elements of marker 52 are known, numerical values of the vectors of the different possible orientations may be precalculated and stored by processor 26. The vectors may be stored in any convenient format known in the art, for example related to a cylindrical coordinate system, or to a spherical coordinate system, or to another Cartesian set of axes, rather than the Cartesian axes presented here. All such formats are assumed to be comprised within the scope of the present invention.

Figure 4:
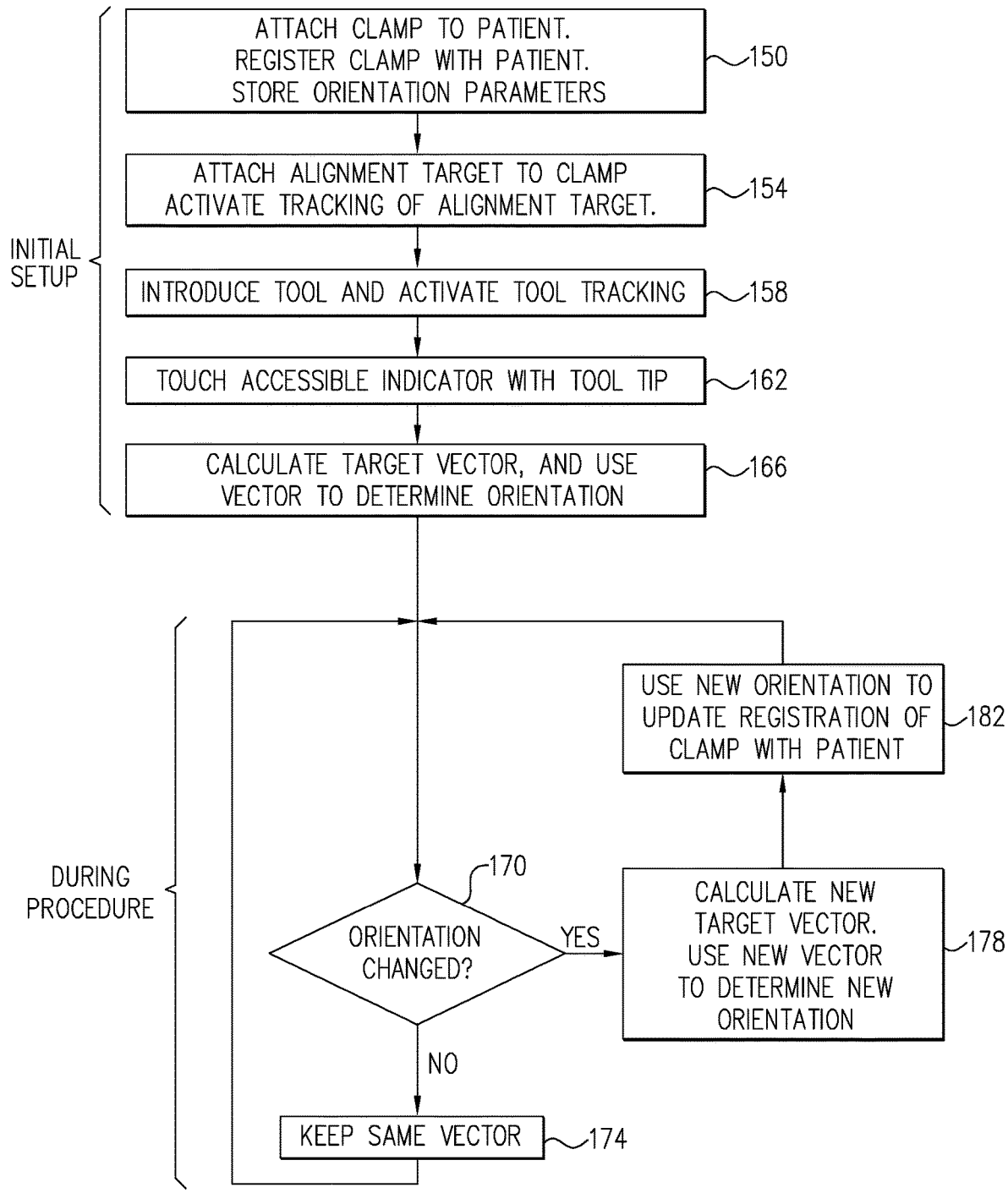
FIG. 4 is a flowchart describing the use of the marker in the medical procedure, according to an embodiment of the present invention.

FIG. 4 is a flowchart describing the use of marker 52 in the medical procedure referred to above, according to an embodiment of the present invention.

In an initial step 150, professional 22 attaches clamp 34 to a bone of patient 30, herein assumed to comprise a spinous process of the patient, by rotating screw 80. The clamp is registered to the patient, typically by a CT (computerized tomography) scan. A method for registering a clamp to a patient is provided in U.S. patent application Ser. No. 16/524,258, which is incorporated herein by reference. Also in the initial step, the preselected point on the target (referred to above) and vector parameters for the four orientations of marker 52, corresponding to the values in Table I, are stored by processor 26.

In a target attachment step 154, the professional uses screw 98 to attach alignment target 48 to the clamp, in one of the four orientations illustrated in FIGS. 3A-3D. It will be understood that depending on the orientation selected, the professional may or may not use adapter 40 for the attachment.

Once alignment target 48 is attached to the clamp, camera 68 and projector 69 are activated, so that processor begins to track the alignment target and the preselected point in the target.

In a tool activation step 158, professional 22 introduces tool 46 into proximity with the patient, and initiates tracking of the tool. The tracking uses tool marker 50, and images of the marker generated in camera 68 from radiation of projector 69. The tracking provides processor 26 with the position of tool tip 54.

In an indicator access step 162, professional 22 touches tool tip 54 on the single indicator, i.e., indicator 118, 168, or 172, that is accessible by virtue of the orientation of target 48 formed in step 154. Processor 26 may recognize that the indicator is being touched by any convenient method known in the art, for example by the tool tip being held on, or in proximity to, the indicator for a preselected period of time, and/or by the tool tip being within a preselected region of the tracked alignment target.

In an orientation calculation step 166, from coordinates of the accessible indicator position and of the preselected point position in the tracked alignment target the processor calculates coordinates of the vector parameters (as in Table I) joining the positions, and from the parameters stored in step 150, identifies the orientation of step 154.

Step 166 completes an initial setup set of steps of the flowchart. The remaining steps are performed as the procedure being performed by professional 26 continues.

Control in the flowchart passes to a decision step 170, where the processor iteratively checks if a change of orientation of the alignment target has occurred. Typically, the change is effected by professional 26 removing then re-attaching the target to clamp 34.

The processor may perform its check by issuing a request, after a preset time period has passed, to the professional to touch tool tip 54 on the single accessible indicator. Alternatively or additionally the professional may inform the processor that a change has been made by any convenient method known in the art, for example by placing tool tip 54 on the single accessible indicator for the preselected period of time referred co above.

If decision step 170 returns negative, i.e., the processor finds there is no change in the target orientation, then in a no change step 174, the processor continues using the existing vector, and control returns to decision step 170.

If decision step 170 returns positive, i.e., the processor finds there is a change in the target orientation then in a change vector step 178 the processor calculates the new coordinates of the new target vector, as described in step 166. The processor uses the new vector to determine the new orientation of the target, and uses the new orientation to continue tracking the target.

In an update registration step 182, the processor uses the new orientation to update the registration of clamp 34 with patient 30. Control then returns to decision step 170.

Figure 5:
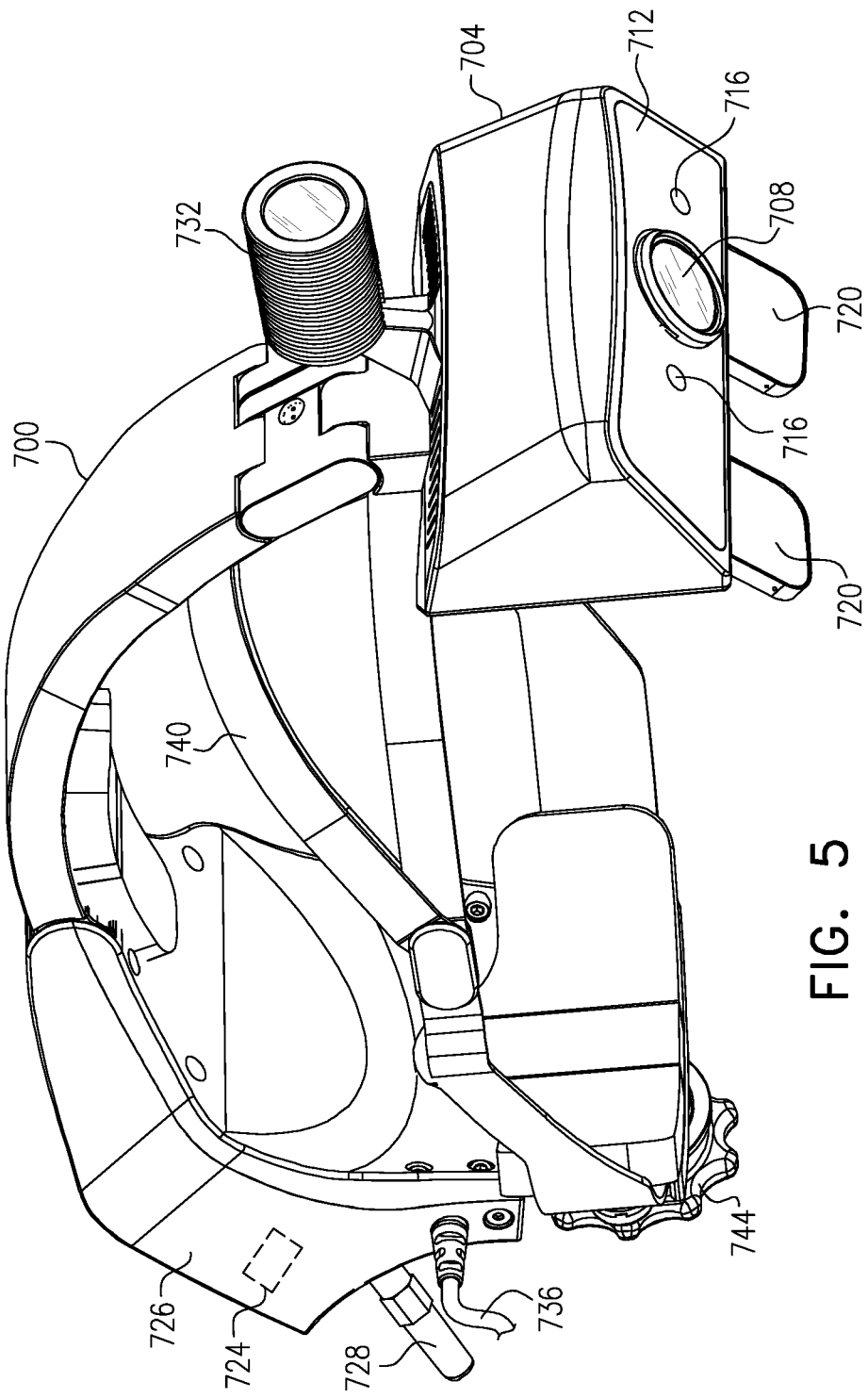
FIG. 5 is a schematic illustration of a head-up display (HUD), according to an embodiment of the present invention.

FIG. 5 is a schematic figure illustrating a head-up display (HUD) 700, according to art embodiment of the present invention. HUD 700 is worn by professional 22, and may be used in place of assembly 24 (FIG. 1). HUD 700 comprises an optics housing 704 which incorporates an infrared camera 708. Housing 704 also comprises an infrared transparent window 712, and within the housing, i.e., behind the window, are mounted one or more infrared projectors 716. Mounted on housing 704 are a pair of augmented reality displays 720, which allow professional 22 to view entities, such as part or all of patient 30 through the displays, and which are also configured to present to the professional images that may be received from database 38 or any other information.

The HUD includes a processor 724, mounted in a processor housing 726, which operates elements of the HUD. Processor 724 typically communicates with processor 26 via an antenna 728, although in some embodiments processor 724 may perform some of the functions performed by processor 26, and in other embodiments may completely replace processor 26.

Mounted on the front of HUD 700 is a flashlight 732. The flashlight projects visible spectrum light onto objects so that professional 22 is able to clearly see the objects through displays 720. Elements of the head-up display are typically powered by a battery (not shown in the figure) which supplies power to the elements via a battery cable in-out 736.

HUD 700 is held in place on the head of professional 22 by a head strap 740, and the professional may adjust the head strap by an adjustment knob 741. It will be understood that although the above description refers to a group of discrete orientations comprising the angles of 0°, 90°, 180°, and 270°, those having ordinary skill in the art will be able to adapt the description, mutatis mutandis, for other groups of discrete orientations, such as 0°, 60°, 120°, and 180°, and all such groups are considered to be comprised within the scope of the present invention.

While the description above assumes that anchoring device 34 comprises a clamp, it will be understood that the anchoring device may comprise other types of attachment to the bone of patient 30, such as a pin that is inserted into the bone. Thus, the scope of the present invention includes all such types of attachment.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A patient marker for image guided surgery configured to be coupled to an anchoring device via a base, the base having a base axis, base connections and a first indicator, the patient marker comprising:
   an adapter having a first surface comprising first surface adapter connections configured to mate with the base connections, and a second surface, opposite the first surface, having second surface adapter connections congruent with the base connections, and at least one second indicator; and
   an alignment target, comprising:
      a target region having an alignment pattern formed thereon; and
      a socket connected to the target region and having socket connections congruent with the first surface adapter connections, so that:
         in a first configuration of the marker, the socket is coupled to the base by mating the first surface adapter connections with the base connections and mating the socket connections with the second surface adapter connections, and
         in a second configuration of the marker, the socket is fit onto the base by mating the socket connections with the base connections,
   whereby an angle of orientation of the alignment target about the base axis is indicated by one of the first indicator and the at least one second indicator.

2. The patient marker according to claim 1, wherein in any given configuration of the marker, only one of the first indicator and the at least one second indicator is accessible.

3. The patient marker according to claim 1, wherein in the first configuration the alignment target fits to the adapter in a plurality of discrete orientations.

4. The patient marker according to claim 3, wherein the discrete orientations comprise two orientations at 180° to each other.

5. The patient marker according to claim 1, wherein in the second configuration the alignment target fits to the base in a plurality of discrete orientations.

6. The patient marker according to claim 5, wherein the discrete orientations comprise two orientations at 180° to each other.

7. The patient marker according to claim 1, wherein in the first configuration the angle of orientation comprises a first pair of angles at 180° to each other, and in the second configuration the angle of orientation comprises a second pair of angles at 180° to each other and at 90° to the first pair of angles.

8. The patient marker according to claim 1, wherein the base connections and the first surface adapter connections are configured so that the adapter mates with the base in one single orientation.

9. The patient marker according to claim 1, wherein the at least one second indicator is a divot that acts as a verification point.

10. The patient marker according to claim 1, wherein the at least one second indicator is formed as an extension of a surface of the adapter.

11. The patient marker according to claim 1, wherein one of the at least one second indicator is positioned so that it aligns with and prevents access to the first indicator, while the first surface adapter connections are mated with the base connections.

12. The patient marker according to claim 1, wherein the at least one second indicator comprises two indicators.

13. The patient marker according to claim 12, wherein the angle between lines from each of the two indicators to a central hole of the adapter is obtuse.

14. The patient marker according to claim 1, wherein the at least one second indicator is configured to be touched by a tip of a tool used in the surgery.

15. A patient marker for image guided surgery configured to be coupled to an anchoring device via a base, the base having a base axis, base connections and a first indicator, the patient marker comprising:
   an adapter having a first surface comprising first surface adapter connections configured to mate with the base connections, and a second surface, opposite the first surface, having second surface adapter connections congruent with the base connections, and at least one second indicator; and
   an alignment target, comprising:
      a target region having an alignment pattern formed thereon; and
      a socket connected to the target region and having socket connections congruent with the first surface adapter connections, so that:
         in a first configuration of the marker, the socket is coupled to the base by mating the first surface adapter connections with the base connections and mating the socket connections with the second surface adapter connections, and
         in a second configuration of the marker, the socket is fit onto the base by mating the socket connections with the base connections,
      wherein one of the at least one second indicator is positioned so that it aligns with and prevents access to the first indicator, while the first surface adapter connections are mated with the base connections.

16. The patient marker according to claim 15, wherein in any given configuration of the marker, only one of the first indicator and the at least one second indicator is accessible.

17. The patient marker according to claim 16, wherein an angle of orientation of the alignment target about the base axis is indicated by one of the first indicator and the at least one second indicator.

18. The patient marker according to claim 15, wherein in the first configuration the alignment target fits to the adapter in a plurality of discrete orientations, and wherein in the second configuration the alignment target fits to the base in a plurality of discrete orientations.

* * * * *

UNITED STATES PATENT AND TRADEMARK OFFICE
CERTIFICATE OF CORRECTION

PATENT NO. : 12,150,821 B2  
APPLICATION NO. : 17/388064  
DATED : November 26, 2024  
INVENTOR(S) : Tomer Gera Page 1 of 1

It is certified that error appears in the above-identified patent and that said Letters Patent is hereby corrected as shown below:

In the Specification

In Column 3, Line 34, delete "3B, 35, and" and insert --3B, 3C, and--.

In Column 6, Line 57, delete "FIGS. 23, 2C," and insert --FIGS. 2B, 2C,--.

In Column 7, Line 54, delete "FIG. 25 illustrates" and insert --FIG. 2C illustrates--.

Signed and Sealed this  
Fourth Day of March, 2025

Coke Morgan Stewart  
*Acting Director of the United States Patent and Trademark Office*